US011679077B2

(12) United States Patent
Deem et al.

(10) Patent No.: US 11,679,077 B2
(45) Date of Patent: *Jun. 20, 2023

(54) SYSTEMS AND METHODS FOR DELIVERY OF A THERAPEUTIC AGENT

(71) Applicant: The Foundry, LLC, Menlo Park, CA (US)

(72) Inventors: Mark E. Deem, Mountain View, CA (US); Hanson Gifford, Woodside, CA (US)

(73) Assignee: The Foundry, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/151,938

(22) Filed: Jan. 19, 2021

(65) Prior Publication Data

US 2021/0186866 A1    Jun. 24, 2021

Related U.S. Application Data

(60) Continuation of application No. 16/842,209, filed on Apr. 7, 2020, now Pat. No. 10,894,011, which is a continuation of application No. 16/659,893, filed on Oct. 22, 2019, now Pat. No. 10,610,675, which is a continuation of application No. 16/036,381, filed on Jul. 16, 2018, now Pat. No. 10,729,897, which is a continuation of application No. 15/358,187, filed on Nov. 22, 2016, now Pat. No. 10,022,529, which is a continuation of application No. 14/601,529, filed on Jan. 21, 2015, now Pat. No. 9,498,283, which is a continuation of application No. 13/660,629, filed on Oct. 25, 2012, now Pat. No. 8,961,391, which is a continuation of application No. 13/253,595, filed on Oct. 5, 2011, now Pat. No. 8,338,164, which is a continuation of application No. 12/559,278, filed on Sep. 14, 2009, now Pat. No. 8,133,497, which is a
(Continued)

(51) Int. Cl.
| | |
|---|---|
| C12M 1/00 | (2006.01) |
| A61K 9/00 | (2006.01) |
| A61K 38/16 | (2006.01) |
| A61K 38/48 | (2006.01) |
| A61K 41/00 | (2020.01) |
| A61N 1/32 | (2006.01) |
| A61N 1/08 | (2006.01) |
| A61N 1/30 | (2006.01) |
| A61N 7/00 | (2006.01) |
| A61B 18/14 | (2006.01) |
| A61B 18/18 | (2006.01) |
| A61N 5/10 | (2006.01) |
| A61M 37/00 | (2006.01) |
| A61B 18/00 | (2006.01) |

(52) U.S. Cl.
CPC ........ *A61K 9/0021* (2013.01); *A61B 18/1492* (2013.01); *A61B 18/1815* (2013.01); *A61K 9/0078* (2013.01); *A61K 38/164* (2013.01); *A61K 38/168* (2013.01); *A61K 38/4893* (2013.01); *A61K 41/00* (2013.01); *A61K 41/0028* (2013.01); *A61K 41/0047* (2013.01); *A61M 37/00* (2013.01); *A61M 37/0092* (2013.01); *A61N 1/08* (2013.01); *A61N 1/303* (2013.01); *A61N 1/327* (2013.01); *A61N 5/10* (2013.01); *A61N 7/00* (2013.01); *C12Y 304/24069* (2013.01); *A61B 2018/0016* (2013.01); *A61B 2018/00214* (2013.01); *A61B 2018/00434* (2013.01); *A61B 2018/1861* (2013.01); *A61M 2210/1035* (2013.01); *A61N 2007/003* (2013.01); *Y02A 50/30* (2018.01)

(58) Field of Classification Search
CPC .................................................. A61K 9/0021
See application file for complete search history.

(56) References Cited

U.S. PATENT DOCUMENTS

| | | |
|---|---|---|
| 1,695,107 A | 12/1928 | Kahl |
| 2,566,806 A | 9/1951 | Miller |
| 3,463,149 A | 8/1969 | Albu et al. |

(Continued)

FOREIGN PATENT DOCUMENTS

| | | |
|---|---|---|
| CA | 2152002 A1 | 12/1995 |
| EP | 3248612 A1 | 11/2017 |

(Continued)

OTHER PUBLICATIONS

Ahnert-Hilger., et al., "Introduction of Macromolecules into Bovine Adrenal-Medullary Chromaffin Cells and Rat Pheochromocytoma Cells (PC12) by Permeabilization with Streptolysin O: Inhibitory Effect of Teanus Toxin on Catecholamine Secretion," J. Neurochem, Jun. 1989, vol. 52 (6), pp. 1751-1758.

(Continued)

*Primary Examiner* — Albert M Navarro
(74) *Attorney, Agent, or Firm* — Merchant & Gould P.C.

(57) ABSTRACT

Methods and apparatus are provided for applying an fragment of a neurotoxin such as the active light chain (LC) of the botulinum toxin (BoNT), such as one of the serotype A, B, C, D, E, F or G botulinum toxins, via permeabilization of targeted cell membranes to enable translocation of the botulinum neurotoxin light chain (BoNT-LC) molecule across the targeted cell membrane to the cell cytosol where a therapeutic response is produced in a mammalian system. The methods and apparatus include use of catheter based delivery systems, non-invasive delivery systems, and transdermal delivery systems.

15 Claims, 27 Drawing Sheets

Related U.S. Application Data division of application No. 11/459,090, filed on Jul. 21, 2006, now Pat. No. 7,608,275.

(60) Provisional application No. 60/702,077, filed on Jul. 22, 2005.

(56) References Cited

U.S. PATENT DOCUMENTS

| | | |
|---|---|---|
| 3,469,139 A | 9/1969 | Colvin et al. |
| 3,788,296 A | 1/1974 | Klatt et al. |
| 3,918,449 A | 11/1975 | Pistor |
| 4,658,836 A | 4/1987 | Turner |
| 4,767,402 A | 8/1988 | Kost et al. |
| 4,976,710 A | 12/1990 | Mackin |
| 5,056,529 A | 10/1991 | De Groot |
| 5,139,029 A | 8/1992 | Fishman et al. |
| 5,158,536 A | 10/1992 | Sekins et al. |
| 5,192,290 A | 3/1993 | Hilal |
| 5,286,254 A | 2/1994 | Shapland et al. |
| 5,304,120 A | 4/1994 | Crandell et al. |
| 5,331,947 A | 7/1994 | Shturman |
| 5,336,178 A | 8/1994 | Kaplan et al. |
| 5,409,483 A | 4/1995 | Campbell et al. |
| 5,432,092 A | 7/1995 | Bailey et al. |
| 5,496,304 A | 3/1996 | Chasan |
| 5,562,608 A | 10/1996 | Sekins et al. |
| 5,766,605 A | 6/1998 | Sanders et al. |
| 5,807,306 A | 9/1998 | Shapland et al. |
| 5,817,073 A | 10/1998 | Krespi |
| 5,820,589 A | 10/1998 | Torgerson et al. |
| 5,843,088 A | 12/1998 | Barra et al. |
| 5,860,974 A | 1/1999 | Abele |
| 5,902,268 A | 5/1999 | Saab |
| 5,957,961 A | 9/1999 | Maguire et al. |
| 5,964,223 A | 10/1999 | Baran |
| 5,972,026 A | 10/1999 | Laufer et al. |
| 6,033,397 A | 3/2000 | Laufer et al. |
| 6,056,744 A | 5/2000 | Edwards |
| 6,063,768 A | 5/2000 | First |
| 6,139,845 A | 10/2000 | Donovan |
| 6,200,333 B1 | 3/2001 | Laufer |
| 6,216,704 B1 | 4/2001 | Ingle et al. |
| 6,265,379 B1 | 7/2001 | Donovan |
| 6,283,989 B1 | 9/2001 | Laufer et al. |
| 6,299,633 B1 | 10/2001 | Laufer |
| 6,302,780 B1 | 10/2001 | Ahn et al. |
| 6,306,423 B1 | 10/2001 | Donovan et al. |
| 6,322,559 B1 | 11/2001 | Daulton et al. |
| 6,358,926 B2 | 3/2002 | Donovan |
| 6,361,554 B1 | 3/2002 | Brisken |
| 6,383,509 B1 | 5/2002 | Donovan et al. |
| 6,411,852 B1 | 6/2002 | Danek et al. |
| 6,425,887 B1 | 7/2002 | McGuckin et al. |
| 6,432,092 B2 | 8/2002 | Miller |
| 6,447,785 B1 | 9/2002 | Donovan |
| 6,448,231 B2 | 9/2002 | Graham |
| 6,464,680 B1 | 10/2002 | Brisken et al. |
| 6,475,160 B1 | 11/2002 | Sher |
| 6,488,673 B1 | 12/2002 | Laufer et al. |
| 6,506,399 B2 | 1/2003 | Donovan |
| 6,526,976 B1 | 3/2003 | Baran |
| 6,546,932 B1 | 4/2003 | Nahon et al. |
| 6,562,057 B2 | 5/2003 | Santin |
| 6,601,581 B1 | 8/2003 | Babaev |
| 6,620,415 B2 | 9/2003 | Donovan |
| 6,623,742 B2 | 9/2003 | Voet |
| 6,626,855 B1 | 9/2003 | Weng et al. |
| 6,632,440 B1 | 10/2003 | Quinn et al. |
| 6,634,363 B1 | 10/2003 | Danek et al. |
| 6,645,496 B2 | 11/2003 | Aoki et al. |
| 6,649,161 B1 | 11/2003 | Donovan |
| 6,658,279 B2 | 12/2003 | Swanson et al. |
| 6,719,694 B2 | 4/2004 | Weng et al. |
| 6,740,321 B1 | 5/2004 | Donovan |
| 6,767,544 B2 | 7/2004 | Brooks et al. |
| 6,770,070 B1 | 8/2004 | Balbierz |
| 6,773,711 B2 | 8/2004 | Voet et al. |
| 6,776,991 B2 | 8/2004 | Naumann |
| 6,827,931 B1 | 12/2004 | Donovan |
| 6,838,434 B2 | 1/2005 | Voet |
| 6,841,156 B2 | 1/2005 | Aoki et al. |
| 6,843,998 B1 | 1/2005 | Steward et al. |
| 6,846,312 B2 | 1/2005 | Edwards et al. |
| 6,847,849 B2 | 1/2005 | Mamo et al. |
| 6,861,058 B2 | 3/2005 | Aoki et al. |
| 6,872,397 B2 | 3/2005 | Aoki et al. |
| 6,917,834 B2 | 7/2005 | Koblish et al. |
| 6,974,578 B1 | 12/2005 | Aoki et al. |
| 7,027,869 B2 | 4/2006 | Danek et al. |
| 7,184,811 B2 | 2/2007 | Phan et al. |
| 7,371,231 B2 | 5/2008 | Rioux et al. |
| 7,462,179 B2 | 12/2008 | Edwards et al. |
| 7,608,275 B2 | 10/2009 | Deem et al. |
| 7,628,789 B2 | 12/2009 | Soltesz et al. |
| 7,655,243 B2 | 2/2010 | Deem et al. |
| 7,747,324 B2 | 6/2010 | Errico et al. |
| 7,853,331 B2 | 12/2010 | Kaplan et al. |
| 8,007,495 B2 | 8/2011 | McDaniel et al. |
| 8,088,127 B2 | 1/2012 | Mayse et al. |
| 8,105,817 B2 | 1/2012 | Deem et al. |
| 8,133,497 B2 | 3/2012 | Deem et al. |
| 8,172,827 B2 | 5/2012 | Deem et al. |
| 8,226,638 B2 | 7/2012 | Mayse et al. |
| 8,338,164 B2 | 12/2012 | Deem et al. |
| 8,483,831 B1 | 7/2013 | Hlavka et al. |
| 8,489,192 B1 | 7/2013 | Hlavka et al. |
| 8,636,684 B2 | 1/2014 | Deem et al. |
| 8,731,672 B2 | 5/2014 | Hlavka et al. |
| 8,740,895 B2 | 6/2014 | Mayse et al. |
| 8,777,943 B2 | 7/2014 | Mayse et al. |
| 8,808,280 B2 | 8/2014 | Mayse et al. |
| 8,821,489 B2 | 9/2014 | Mayse et al. |
| 8,911,439 B2 | 12/2014 | Mayse et al. |
| 8,932,289 B2 | 1/2015 | Mayse et al. |
| 8,961,391 B2 | 2/2015 | Deem et al. |
| 8,961,507 B2 | 2/2015 | Mayse et al. |
| 8,961,508 B2 | 2/2015 | Mayse et al. |
| 9,005,195 B2 | 4/2015 | Mayse et al. |
| 9,017,324 B2 | 4/2015 | Mayse et al. |
| 9,125,643 B2 | 9/2015 | Hlavka et al. |
| 9,149,328 B2 | 10/2015 | Dimmer et al. |
| 9,339,618 B2 | 5/2016 | Deem et al. |
| 9,498,283 B2 | 11/2016 | Deem et al. |
| 9,511,210 B2 | 12/2016 | Deem et al. |
| 9,700,707 B2 | 7/2017 | Deem et al. |
| 10,022,529 B2 | 7/2018 | Deem et al. |
| 10,052,465 B2 | 8/2018 | Deem et al. |
| 10,610,675 B2 | 4/2020 | Deem et al. |
| 10,729,897 B2 | 8/2020 | Deem et al. |
| 10,894,011 B2 | 1/2021 | Deem et al. |
| 2001/0044596 A1 | 11/2001 | Jaafar |
| 2002/0013581 A1 | 1/2002 | Edwards et al. |
| 2002/0082197 A1 | 6/2002 | Aoki et al. |
| 2002/0087208 A1 | 7/2002 | Koblish et al. |
| 2002/0111620 A1 | 8/2002 | Cooper et al. |
| 2002/0143302 A1 | 10/2002 | Hinchliffe et al. |
| 2002/0198512 A1 | 12/2002 | Seward |
| 2003/0018344 A1 | 1/2003 | Kaji et al. |
| 2003/0023287 A1 | 1/2003 | Edwards et al. |
| 2003/0036755 A1 | 2/2003 | Ginn |
| 2003/0050591 A1 | 3/2003 | Patrick McHale |
| 2003/0113349 A1 | 6/2003 | Coleman, III |
| 2003/0118327 A1 | 6/2003 | Um et al. |
| 2003/0153881 A1 | 8/2003 | Roche et al. |
| 2003/0159700 A1 | 8/2003 | Laufer et al. |
| 2003/0202990 A1 | 10/2003 | Donovan et al. |
| 2003/0211121 A1 | 11/2003 | Donovan |
| 2003/0233099 A1 | 12/2003 | Danaek et al. |
| 2004/0009180 A1 | 1/2004 | Donovan |
| 2004/0010290 A1 | 1/2004 | Schroeppel et al. |
| 2004/0028676 A1 | 2/2004 | Klein et al. |
| 2004/0086531 A1 | 5/2004 | Barron |
| 2004/0091880 A1 | 5/2004 | Wiebusch et al. |
| 2004/0142005 A1 | 7/2004 | Brooks et al. |

(56) References Cited

U.S. PATENT DOCUMENTS

| | | |
|---|---|---|
| 2004/0151741 A1 | 8/2004 | Borodic |
| 2004/0175399 A1 | 9/2004 | Schiffman |
| 2004/0186435 A1 | 9/2004 | Seward |
| 2004/0213813 A1 | 10/2004 | Ackerman |
| 2004/0213814 A1 | 10/2004 | Ackerman |
| 2004/0220562 A1 | 11/2004 | Garabedian et al. |
| 2004/0226556 A1 | 11/2004 | Deem et al. |
| 2004/0248188 A1 | 12/2004 | Sanders |
| 2004/0253274 A1 | 12/2004 | Voet |
| 2005/0007441 A1 | 1/2005 | Hyuga |
| 2005/0019346 A1 | 1/2005 | Boulis |
| 2005/0065575 A1 | 3/2005 | Dobak |
| 2005/0074461 A1 | 4/2005 | Donovan |
| 2005/0107853 A1 | 5/2005 | Krespi et al. |
| 2005/0152924 A1 | 7/2005 | Voet |
| 2005/0182393 A1 | 8/2005 | Abboud et al. |
| 2005/0183732 A1 | 8/2005 | Edwards |
| 2005/0240147 A1 | 10/2005 | Makower et al. |
| 2005/0245926 A1 | 11/2005 | Edwards et al. |
| 2005/0281751 A1 | 12/2005 | Levin |
| 2006/0004323 A1 | 1/2006 | Chang et al. |
| 2006/0008462 A1 | 1/2006 | Sanders |
| 2006/0084966 A1 | 4/2006 | Maguire et al. |
| 2006/0106361 A1 | 5/2006 | Muni et al. |
| 2006/0153876 A1 | 7/2006 | Sanders |
| 2006/0222667 A1 | 10/2006 | Deem et al. |
| 2006/0225742 A1 | 10/2006 | Deem et al. |
| 2006/0254600 A1 | 11/2006 | Danek et al. |
| 2007/0021803 A1 | 1/2007 | Deem et al. |
| 2007/0025919 A1 | 2/2007 | Deem et al. |
| 2007/0043350 A1 | 2/2007 | Soltesz et al. |
| 2007/0083194 A1 | 4/2007 | Kunis et al. |
| 2007/0100390 A1 | 5/2007 | Danaek et al. |
| 2007/0106292 A1 | 5/2007 | Kaplan et al. |
| 2007/0118184 A1 | 5/2007 | Danek et al. |
| 2007/0129720 A1 | 6/2007 | Demarais et al. |
| 2007/0156185 A1 | 7/2007 | Swanson et al. |
| 2007/0250050 A1 | 10/2007 | Lafontaine |
| 2007/0267011 A1 | 11/2007 | Deem et al. |
| 2007/0270794 A1 | 11/2007 | Anderson et al. |
| 2008/0021369 A1 | 1/2008 | Deem et al. |
| 2008/0051839 A1 | 2/2008 | Libbus et al. |
| 2008/0091379 A1 | 4/2008 | Lynch et al. |
| 2008/0161890 A1 | 7/2008 | Lafontaine |
| 2008/0255642 A1 | 10/2008 | Zarins et al. |
| 2008/0312725 A1 | 12/2008 | Penner |
| 2009/0018538 A1 | 1/2009 | Webster et al. |
| 2009/0043301 A1 | 2/2009 | Jarrard et al. |
| 2009/0177192 A1 | 7/2009 | Rioux et al. |
| 2009/0221997 A1 | 9/2009 | Arnold et al. |
| 2010/0003282 A1 | 1/2010 | Deem et al. |
| 2010/0087775 A1 | 4/2010 | Deem et al. |
| 2011/0118725 A1 | 5/2011 | Mayse et al. |
| 2011/0152855 A1 | 6/2011 | Mayse et al. |
| 2011/0257647 A1 | 10/2011 | Mayse et al. |
| 2011/0301587 A1 | 12/2011 | Deem et al. |
| 2012/0016363 A1 | 1/2012 | Mayse et al. |
| 2012/0016364 A1 | 1/2012 | Mayse et al. |
| 2012/0029261 A1 | 2/2012 | Deem et al. |
| 2012/0158101 A1 | 6/2012 | Stone et al. |
| 2012/0203216 A1 | 8/2012 | Mayse et al. |
| 2012/0203222 A1 | 8/2012 | Mayse et al. |
| 2012/0209261 A1 | 8/2012 | Mayse et al. |
| 2012/0209296 A1 | 8/2012 | Mayse et al. |
| 2012/0302909 A1 | 11/2012 | Mayse et al. |
| 2012/0310233 A1 | 12/2012 | Dimmer et al. |
| 2012/0316552 A1 | 12/2012 | Mayse et al. |
| 2012/0316559 A1 | 12/2012 | Mayse et al. |
| 2013/0123751 A1 | 5/2013 | Deem et al. |
| 2013/0289555 A1 | 10/2013 | Mayse et al. |
| 2013/0289556 A1 | 10/2013 | Mayse et al. |
| 2013/0303948 A1 | 11/2013 | Deem et al. |
| 2013/0310822 A1 | 11/2013 | Mayse et al. |
| 2014/0186341 A1 | 7/2014 | Mayse |
| 2014/0257271 A1 | 9/2014 | Mayse et al. |
| 2014/0276792 A1 | 9/2014 | Kaveckis et al. |
| 2015/0051597 A1 | 2/2015 | Mayse et al. |
| 2015/0141985 A1 | 5/2015 | Mayse et al. |
| 2015/0190193 A1 | 7/2015 | Mayse et al. |
| 2015/0366603 A1 | 12/2015 | Hlavka et al. |
| 2016/0022351 A1 | 1/2016 | Kaveckis et al. |
| 2016/0038725 A1 | 2/2016 | Mayse et al. |
| 2019/0083768 A1 | 3/2019 | Deem et al. |
| 2020/0360677 A1 | 11/2020 | Deem et al. |

FOREIGN PATENT DOCUMENTS

| | | |
|---|---|---|
| JP | 2002145784 A | 5/2002 |
| WO | WO-9119529 A1 | 12/1991 |
| WO | WO-9519805 A1 | 7/1995 |
| WO | WO-9934831 A1 | 7/1999 |
| WO | WO-0062699 A2 | 10/2000 |
| WO | WO-2004006954 A2 | 1/2004 |
| WO | WO-2004048519 A2 | 6/2004 |
| WO | WO-2004077987 A1 | 9/2004 |
| WO | WO-2004101028 A2 | 11/2004 |
| WO | WO-2005032646 A2 | 4/2005 |
| WO | WO-2005048988 A1 | 6/2005 |
| WO | WO-2004101028 A3 | 12/2006 |
| WO | WO-2007014003 A2 | 2/2007 |

OTHER PUBLICATIONS

"Anonymous: Neurotoxin (from Wikipedia)," Retrieved from http://en.wikipedia.org/w/index.php?title=Neurotoxin&printable=yes, Apr. 2, 2015, 23 pages.

Application and File History for U.S. Appl. No. 16/659,893, filed Oct. 22, 2019, Inventors: Deem et al.

Application and File History for U.S. Appl. No. 16/842,209, filed Apr. 7, 2020, Inventors: Deem et al.

Bigalke., et al., "Clostridial Neurotoxins," Handbook of Experimental Pharmacology (Aktories, K. and Just, I., eds), 2000, vol. 145, pp. 407-443.

Bittner., et al., "Isolated Light Chains of Botulinum Neurotoxins Inhibit Exocytosis," The Journal of Biological Chemistry, 1989, vol. 264(18), pp. 10354-10360.

Blindt., et al., "Development of a New Biodegradable Intravascular Polymer Stent with Simultaneous Incorporation of Bioactive Substances," The International Journal of Artificial Organs, 1999, vol. 22 (12), pp. 843-853.

Buzzi., "Diphtheria Toxin Treatment of Human Advanced Cancer," Cancer Research, 1982, vol. 42, pp. 2054-2058.

Chaddock., et al., "Expression and Purification of Catalytically Active, Non-Toxic Endopeptidase Derivatives of Clostridium Botulinum Toxin Type A," Protein Expression and Purification, Jul. 2002, vol. 25 (2), pp. 219-228.

Chang., "Cell Poration and Cell Fusion Using an Oscillating Electric Field," Biophys. J, 1989, vol. 56 (4), pp. 641-652.

De Paiva., et al., "Light Chain of Botulinum Neurotoxin is Active in Mammalian Motor Nerve Terminals When Delivered Via Liposomes," FEBS Lett, Dec. 1990, vol. 17:277(1-2), pp. 171-174.

Guzman., et al., "Bioeffects Caused by Changes in Acoustic Cavitation Bubble Density and Cell Concentration: A Unified Explanation Based on Cell-to-Bubble Ratio and Blast Radius," Ultrasound in medicine & biology, 2003, vol. 29 (8), pp. 1211-1222.

Guzman H.R, et al., "Equilibrium Loading of Cells with Macromolecules by Ultrasound: Effects of Molecular Size and Acoustic Energy," J Pharm Sci., Jul. 2002, vol. 91 (7), pp. 1693-1701.

Kistner., et al., "Reductive Cleavage of Tetanus Toxin and Botulinum Neurotoxin A by the Thioredoxin System from Brain," Naunyn-Schmiedebergs Arch Pharmacal, Feb. 1992, vol. 345 (2), pp. 227-234.

Korpela., et al., "Comparison of Tissue Reactions in the Tracheal Mucosa Surrounding a Bioabsorbable and Silicone Airway Stents," Annals of Thoracic Surgery, 1998, vol. 66, pp. 1772-1776.

Kreitman., "Taming Ricin Toxin," Nature Biotechnology, 2003, vol. 21, pp. 372-374.

Raj., "Editorial," Pain Practice, 2004, vol. 4 (1S), pp. S1-S3.

(56) References Cited

OTHER PUBLICATIONS

Schmitt G.S., et al., "Indwelling Transbronchial Catheter Drainage of Pulmonary Abscess," Ann Thorac Surg, Jan. 1988, vol. 45 (1), pp. 43-47.

Shaari., et al., "Rhinorrhea is Decreased in Dogs After Nasal Application of Botulinum Toxin," Otolaryngol Head Neck Surgery, Apr. 1995, vol. 112 (4), pp. 566-571.

Simpson., et al., "Isolation and Characterization of the botulinum Neurotoxins," Methods Enzymol, 1988, vol. 165, pp. 76-85.

Simpson L.L., "The Origin, Structure, and Pharmacological Activity of Botulinum Toxin," Pharmacol Reviews, Sep. 1981, vol. 33 (3), pp. 155-188.

Sundaram, et al., "An Experimental and Theoretical Analysis of Ultrasound-Induced Permeabilization of Cell Membranes," Biophysical Journal, May 2003, vol. 84 (5), pp. 3087-3101.

Tsuji., et al., "Biodegradable Stents as a Platform to Drug Loading," International Journal of Cardiovascular Interventions, 2003, vol. 5(1), pp. 13-16.

Unal., et al., "Effect of Botulinum Toxin Type A on Nasal Symptoms in Patients with Allergic Rhinitis: A Double-blind, Placebo-controlled Clinical Trial," Acta Oto-Laryngologica, Dec. 2003, vol. 123 (9), pp. 1060-1063.

Weaver, "Electroporation: A General Phenomenon for Manipulating Cells and Tissues," Journal of Cellular Biochemistry, Apr. 1993, vol. 51(4), pp. 426-435.

SYSTEMS AND METHODS FOR DELIVERY OF A THERAPEUTIC AGENT

RELATED APPLICATIONS

This application is a continuation of application Ser. No. 16/842,209 filed Apr. 7, 2020, which in turn is a continuation of application Ser. No. 16/659,893 filed Oct. 22, 2019, now U.S. Pat. No. 10,610,675 issued Apr. 7, 2020, which in turn is a continuation of application Ser. No. 16/036,381 filed Jul. 16, 2018, now U.S. Pat. No. 10,729,897 issued Aug. 4, 2020, which in turn is a continuation of application Ser. No. 15/358,187 filed Nov. 22, 2016, now U.S. Pat. No. 10,022,529 issued Jul. 17, 2018, which in turn is a continuation of application Ser. No. 14/601,529 filed Jan. 21, 2015, now U.S. Pat. No. 9,498,283 issued Nov. 22, 2016, which in turn is a continuation of application Ser. No. 13/660,629 filed Oct. 25, 2012, now U.S. Pat. No. 8,961,391 issued Feb. 24, 2015, in turn which is a continuation of application Ser. No. 13/253,595 filed Oct. 5, 2011, now U.S. Pat. No. 8,338,164 issued Dec. 25, 2012, which in turn is a continuation of application Ser. No. 12/559,278 filed Sep. 14, 2009, now U.S. Pat. No. 8,133,497 issued Mar. 13, 2012, which in turn is a divisional of application Ser. No. 11/459,090 filed Jul. 21, 2006, now U.S. Pat. No. 7,608,275 issued Oct. 27, 2009, which claims the benefit of U.S. Provisional Application No. 60/702,077 filed Jul. 22, 2005, each of which is hereby fully incorporated herein by reference. U.S. Pat. No. 7,608,275 also claims the benefit of, and incorporated by reference in its entirety U.S. Provisional Application No. and 60/747,771, filed on May 19, 2006, which is thereby also fully incorporated herein by reference.

BACKGROUND OF THE INVENTION

Field of the Invention

The present invention relates to methods and apparatus for the control of autonomic nerve function comprising delivery via permeabilization of targeted cell membranes a therapeutically effective amount of a portion or fragment of a neurotoxin such as botulinum toxin (BoNT), the active portion known as the light chain (LC), to cause a clinical benefit in various regions within the body. More particularly, the present invention relates to methods and systems for delivering toxins, such as botulinum toxin light chain fragments, to target cells in a nasal cavity.

First used for medical purposes over 20 years ago for treatment of blepharospasm and strabismus and other skeletal muscle abnormalities, certain neurotoxins have found widespread use in millions of patients worldwide for a variety of conditions.

Controlled injection of neurotoxins has become a common procedure to control skeletal muscle spasms. While the primary application of neurotoxins such as BOTOX®, commercially sold by Allergan, Inc. (Irvine, Calif.), has been focused on cosmetic applications, such as treatment of facial wrinkles, other uses for the compound are now common. Certain applications include treatment of cervical dystonia, tremor, headache (migraine), spasticity, torticollis, hemifacial spasm, blepharospasm, meige syndrome, spastic dysphonia, writers cramp, hyperhydrosis, hypersalivation, bladder dysfunction multiple sclerosis, spinal cord injury, cystic fibrosis, stroke paralysis, stuttering, and all types of pain.

*Clostridium botulinum* neurotoxins (BoNTs) block the release of acetylcholine from peripheral cholinergic nerve endings thereby disabling the release of neurotransmitters from the cells (Bigalke, H. and Shoer, L. F. (1999) Clostridial Neurotoxins in Handbook of Experimental Pharmacology 45, 407-443). This mechanism of action is well defined. Seven immunologically distinct serotypes of neurotoxin, designated types A through G, have been identified as discussed by Simpson, L. L., Schmidt, J. J. and Middlebrook, J. L. (1988) in Methods Enzymol. 165, 76-85. There are general structural and functional similarities among the various types of neurotoxins, but they all have preferred recipients, for example some favor use in humans and other in non-human species.

A frequently used neurotoxin for many applications in the human body is Botulinum Toxin Type A (BoNT\A), a protein produced by the bacterium *Clostridium botulinum* and sold commercially by Allergan, Inc., as BOTOX®. Botulinum toxin blocks the release of neurotransmitter from the nerves that control the contraction of the target muscles. When used in medical settings, small doses of the toxin are injected into the affected muscles and block the release of a chemical acetylcholine that signals the muscle to contract. The toxin thus paralyzes or weakens the injected muscle.

In addition, use of neurotoxin for control of the following conditions has been proposed in U.S. Pat. No. 6,063,768 to First, and U.S. Pat. No. 5,766,605 to Sanders, including: rhinorrhea, asthma, COPD, excessive stomach acid secretion, spastic colitis, otitus media, arthritis, tensoynovitis, lupus, connective tissue disease, inflammatory bowel disease, gout, tumors, musculo-skeletal abnormalities, reflex sympathetic dystrophies, tendonitis, bursitis, and peripheral neuropathy. Various other patents contemplate the use of a neurotoxin for additional applications such as, neuromuscular disorders (U.S. Pat. No. 6,872,397), essential tremor (U.S. Pat. No. 6,861,058), pancreatitis (U.S. Pat. No. 6,843,998), muscle spasm (U.S. Pat. No. 6,841,156), sinus headache (U.S. Pat. No. 6,838,434), endocrine disorders (U.S. Pat. No. 6,827,931), priapism (U.S. Pat. No. 6,776,991), thyroiditis (U.S. Pat. No. 6,773,711), cardiovascular disease (U.S. Pat. No. 6,767,544), thyroid disorders (U.S. Pat. No. 6,740,321), hypocalcemia (U.S. Pat. No. 6,649,161), hypercalcemia (U.S. Pat. No. 6,447,785), tardive dyskenesia (U.S. Pat. No. 6,645,496), fibromyalgia (U.S. Pat. No. 6,623,742), Parkinson's Disease (U.S. Pat. No. 6,620,415) cerebral palsy (U.S. Pat. No. 6,448,231), inner ear disorders (U.S. Pat. No. 6,358,926), cancers (U.S. Pat. No. 6,139,845), otic disorders (U.S. Pat. No. 6,265,379), appetite reduction (US2004/0253274), compulsive disorders (US2004/0213814, US2004/0213813), uterine disorders (US2004/0175399), neuropsychiatric disorders (US2003/0211121), dermatological or transdermal applications (US2004/00091880), focal epilepsy (US2003/0202990) the contents of which are expressly incorporated herein by reference in their entirety.

The patent authors have further detailed devices and methods for treating asthma with local delivery of the intact botulinum toxin in U.S. patent application Ser. No. 10/437,882, filed on May 13, 2003, the contents of which are expressly incorporated by reference herein in its entirety.

Due to their extreme toxicity, neurotoxins are highly controlled and can have disastrous consequences if not used and controlled properly, especially when used in vivo. In addition, due to their toxicity, the body tends to build up a resistance to their use, resulting in lower efficacy, the need for increased treatments, or the need to discontinue their use all together in certain patients.

In light of the foregoing, it would be desirable to provide methods and apparatus for delivering neurotoxins such as botulinum toxins non-toxically.

It would also be desirable to provide methods and apparatus for treating various conditions with a neurotoxin such as botulinum toxin fragments via in vivo cell permeabilization.

In would also be desirable to provide a system of devices, including catheters, trocars, needles, endoscopes, inhalers, nebulizers and aerosolizers and other mechanisms to deliver fragmented neurotoxins non-toxically.

Further, it would be desirable to couple energy delivery devices with the delivery of fragmented neurotoxins to deliver active neurotoxins, non-toxically, including catheter based energy systems, and non-invasive energy systems.

For example, rhinitis, which includes the symptoms of rhinorrhea, is a condition resulting from inflammation and swelling of the patient's mucus membranes which line the nasal cavity. Rhinitis and/or rhinorrea can arise from a number of conditions, most often results from allergies to pollen, dust, seasonal allergens or other airborne substances, but can also be caused by anatomic pathologies such as blockages (as in the case of sinusitis). Symptoms may include sneezing, itching, nasal congestion, and a runny nose.

While numerous treatments for rhinitis have been proposed over the years, no single treatment is optimum for all patients or all conditions. Most commonly, hay fever and other forms of rhinitis are treated with antihistamines which block the inflammatory response. While effective, many antihistamines can cause drowsiness, have a limited duration of effect, and present the patient with an on-going cost to continuously purchase the drugs.

Recently, a longer term therapy for rhinitis which relies on the use of botulinum toxin ("BoNT") for blocking mucus production by mucus-producing cells in the nasal membrane has been proposed. Botulinum and other neurotoxins are capable of disabling adrenergic cells, including epithelial or goblet cells which are responsible for the majority of mucus production in the nasal cavity membrane. Dr. Ira Sanders has demonstrated that introduction of intact botulinum toxin molecules into the nasal passages of canines can reduce mucus secretion by a significant amount.

While the experimental work of Dr. Sanders holds promise for long term rhinitis treatment, it faces a number of challenges before it is suitable for wide spread use in humans. In particular, botulinum toxin is a neurotoxin which could have significant negative effects on a patient if accidentally released outside of the targeted nasal passages. Inadvertent distribution of the toxin to muscles of the oropharynx, mouth, tongue, or elsewhere could result in serious complications to the patient. Additionally, the use of botulinum-soaked gauze pads for delivering the toxin to the nasal cavities, as demonstrated by Dr. Sanders, will have limited ability to uniformly and selectively deliver the botulinum to the regions having high concentrations of preferred target cells, such as epithelial or goblet cells in the nasopharynx.

For these reasons, it would be desirable to provide improved methods and systems for delivering toxins, such as botulinum and active botulinum fragments, to the nasal membrane of a patient, particularly a patient suffering from rhinitis or other conditions associated with nasal inflammation and conditions, such as sinus headaches and migraine headaches. The methods and systems should be capable of providing for selective and repeatable delivery of the toxins to defined target areas within the nasal cavities, including particular paranasal sinuses, the nasopharynx, and in some cases substantially the entire nasal cavity. The systems and methods should provide for the safe and effective delivery of the toxins, and in particular should reduce or eliminate the risk of toxin being delivered to non-targeted tissues outside of the nasal cavity. At least some of these objectives will be met by the inventions described herein below.

U.S. Pat. No. 5,766,605, to Sanders et al. has been described above. Sharri et al. (1995) Otolaryngol. Head Neck Surg. 112: 566-571 also reports the work of Dr. Sanders described in the '605 patent. Ünal et al. (2002) Acta Otolaryngol 123: 1060-1063 describes the injection of botulinum toxin A into the turbinates of patients suffering from allergic rhinitis. See also, U.S. Pat. No. 6,974,578. The purification and possible therapeutic uses of botulinum light chain are described in US2004/0151741, US2005/0019346, and Chaddock et al. (2002) Protein Expression and Purification 25: 219-228. Energy-mediated transdermal delivery of intact botulinum toxin is suggested in US2005/007441 and 2004/0009180. The use of catheters and other devices for the energy-mediated delivery of botulinum light chain is described in commonly owned co-pending provisional application 60/702,077, filed Jul. 22, 2005, the full disclosure of which has previously been incorporated herein by reference.

All publications and patents or patent applications mentioned in this specification are herein incorporated by reference to the same extent as if each individual publication, patent or patent application was specifically and individually so incorporated by reference.

BRIEF SUMMARY OF THE INVENTION

According to the present invention, an active fragment (sometimes referred to as a catalytic portion) of a neurotoxin such as the botulinum neurotoxin (BoNT), preferably the light chain (LC) portion of BoNT, is delivered to target cells via cell membrane permeabilization. Such delivery provides a non-toxic delivery scheme for deriving a variety of clinical benefits. Although botulinum toxins are used broadly for a variety of clinical applications, the present invention provides enhanced methods of delivery and use of the isolated active fragments or portions of the toxin. Other neurotoxins which may be used in the methods and systems of the present invention include ricin and its active fragments, exotoxin A and its active fragments, diphtheria toxin and its active fragments, cholera toxin and its active fragments, tetanus toxin and its active fragments, and the like.

The present invention contemplates application to all of the conditions listed herein, collectively defined as "therapeutic target conditions", and any other conditions for which BoNT and other neurotoxins are known to or can be shown to provide a therapeutic benefit. Certain examples have been detailed below for specific applications, but it is within the scope of the present invention that the methods and devices detailed herein have specific applications to many or all of the conditions wherein the intact neurotoxins have shown or proposed to show a therapeutic benefit or effect.

In one aspect of the present invention, BoNT-LC or other active neurotoxin fragment is delivered with the application of energy to achieve cell membrane permeabilization.

In another aspect of the present invention methods and apparatus are provided for altering autonomic nerve function by utilizing an electric field or ultrasonic energy generated by a pulse or pulses of a designated duration and amplitude to alter tissue at the cellular level via permeabilization of the cell membrane to facilitate the translocation of the BoNT-LC or other active neurotoxin fragment to the cell cytosol.

A further aspect of the invention is to provide methods and apparatus for treating or inhibiting a variety of diseases or syndromes that have an underlying neurogenic component, by disrupting the neurogenic activities of the promoters or mediators of the disease or syndrome. Such disruption is facilitated by delivering an active fragment of botulinum toxin, such as the light chain portion of botulinum toxin serotype A (BoNT-LC/A), in the presence of an electric field or ultrasonic energy applied to permeabilize the wall of targeted cell under conditions which induce reversible poration of the cellular membrane and efficient passage of the BoNT-LC fragment to the cell cytosol, its catalytic environment.

In addition to the methods described thus far, the present invention further provides systems for delivering toxins to target cells in a mammalian host. The target cells may be in any of the target regions described above or in any other target region which may benefit from the specific and enhanced delivery of a neurotoxin to cells within the region. Systems comprise catheter or other structure adapted to introduce the toxin or toxin fragment to a region adjacent the target cells. The systems further comprise an energy applicator for applying energy to the target cells under condition which cause poration of the cell membranes to enhance delivery of the toxins and/or their active fragments. The systems still further comprise a source of the toxin or active fragments suitable for introduction from the catheter or other delivery structure.

The energy applicator will typically be adapted to selectively apply energy to target cells within the region where the toxin is to be introduced, e.g., by focusing energy distribution to the particular target cells or regions which are rich with the target cells. Alternatively, the energy applicator may be adapted to apply energy non-selectively within the target region where both target cells and other cell types may receive the energy.

In some instances, the toxin may comprise an intact toxin, but more usually will comprise an active toxin fragment as defined elsewhere in this application. In the exemplary embodiments, the active toxin fragment is the light chain fragment of the botulinum toxin (BoNT-LC). The light chain fragment may be derived from any one of at least botulinum toxins A, B, C, D, E, F, and G. The energy applicators of the systems of the present invention may be adapted to apply electric energy, typically pulses between 1 V and 500 V to the targeted region. The electric energy may be radiofrequency (RF) energy, where the energy may be pulsed for durations between 5 microseconds to 100 milliseconds. Alternatively, the electrical energy can be direct current (DC), alternating current (AC), or combinations thereof.

In addition to electrical energy, the energy applicator may be adapted to deliver ultrasonic energy, X-ray beam energy, microwave energy, or any other energy type which can achieve a reversible poration of the target cell walls.

There are at least two general power categories of medical ultrasound waves which may be utilized in the present invention. One category of medical ultrasound wave is high acoustic pressure ultrasound. Another category of medical ultrasound wave is low acoustic pressure ultrasound. Acoustic power is expressed in a variety of ways by those skilled in the art. One method of estimating the acoustic power of an acoustic wave on tissue is the Mechanical Index. The Mechanical Index (MI) is a standard measure of the acoustic output in an ultrasound system. High acoustic pressure ultrasound systems generally have a MI greater than 10. Low acoustic pressure systems generally have a MI lower than 5. For example, diagnostic ultrasound systems are limited by law to a Mechanical Index not to exceed 1.9. Another measurement used by those skilled in the art is the spatial peak, peak average intensity (Isppa). The intensity of an ultrasound beam is greater at the center of its cross section than at the periphery. Similarly, the intensity varies over a given pulse of ultrasound energy. Isppa is measured at the location where intensity is maximum averaged over the pulse duration. Isppa for high acoustic pressure or high intensity focused ultrasound (HIFU) applications ranges from approximately 1500 W/cm$^2$ to 9000 W/cm$^2$. Diagnostic ultrasound equipment, for instance, will generally have, and an Isppa less than 700 W/cm$^2$. Yet another way in which ultrasound waves can be characterized is by the amplitude of their peak negative pressure. High acoustic pressure or HIFU applications employ waves with peak amplitudes in excess of 10 MPa. Low acoustic pressure ultrasound will generally have peak negative pressures in the range of 0.01 to 5.0 MPa. Diagnostic ultrasound equipment, for example, will generally have a peak amplitude less than 3.0 MPa. Both high and low acoustic pressure ultrasound systems generally operate within the frequency range of 20 KHz-10.0 MHz Interventional applications (such as in blood vessels) operate clinically up to about 50 MHz. Also opthalmologic applications up to about 15 MHz. Diagnostic imaging typically uses frequencies of about 3 to about 10 MHz. Physical therapy ultrasound systems generally operate at frequencies of either 1.0 MHz or 3.3 MHz. High acoustic pressure ultrasound or high intensity focused ultrasound has been used for tissue disruption, for example for direct tumor destruction. High intensity focused ultrasound using high acoustic pressure ultrasound is most commonly focused at a point in order to concentrate the energy from the generated acoustic waves in a relatively small focus of tissue.

Systems and methods for permeabilization of target tissue cell membranes according to the present invention may employ either high acoustic pressure or low acoustic pressure ultrasound. Some embodiments may preferably employ relatively low acoustic pressure, for example the systems described herein where the transducers are mounted on the delivery devices and operate inside the body. Other systems may operate at interim acoustic pressure ranges. For example, systems described herein which employ an external ultrasound generator and transducer and which conduct the ultrasound to the target tissues through the use of a wave guide. In these systems, losses due to transduction through the wave guide can be compensated for by increasing the input power to the wave guide until adequate power is delivered to the target tissue. Finally, some systems described herein may employ focused or partially focused higher pressure ultrasound, for example the systems which employ an external mask to conduct the ultrasonic power through the tissues to the target tissues. It should be appreciated that combinations of high and low acoustic pressure systems may also be employed.

The catheter or other structure may be adapted to introduce the toxin to the target cells in a variety of ways. For example, catheters may comprise a needle for injecting the toxin, optionally a needle which is deployable axially or radially from the catheter body. Alternatively or additionally, catheters may be provided with nozzles or other ports for aerosolizing the toxin, particularly within regions of the lung as described herein. Still further alternatively or additionally, the catheters may comprise balloons or other expandable elements for deflecting an end of the catheter to engage one or more ports on the catheter against the tissue where the toxin fragments are released through the port(s). In a specific embodiment, the ports may be in the balloon itself where the toxin fragments are released through the ports in the balloon as the balloon is inflated with the medium containing the fragments. With such balloon embodiments, the electrodes or other energy transducers will typically be located within the balloon for applying the poration energy to the target tissue. Further optionally, the energy applicators may be mounted directly on the catheters, for example in the form of acoustic transducers, RF or other electrical electrodes, or the like. Alternatively, the energy applicator may be provided separately from the toxin delivery catheter or other source, typically being an external source, such as an external high intensity focused ultrasound (HIFU) source or an external electrode array for delivering radiofrequency or other electroporation energy.

In a further aspect of the invention, it may be desirable to provide methods and devices that utilize a non-toxic delivery mechanism to target cells to reduce the potential for an immunogenic response to the delivered toxin over time.

In a further aspect of the invention, it may be desirable to deliver the therapeutic neurotoxin fragment and energy via a catheter.

In a further aspect of the invention, it may be desirable to deliver the therapeutic neurotoxin fragment via an aerosolizer or nebulizer.

In a further aspect of the invention, it may be desirable to deliver the therapeutic neurotoxin fragment via an inhaler.

In a further aspect of the invention, it may be desirable to deliver the therapeutic neurotoxin fragment and membrane transport energy transdermally.

In a further aspect of the invention, it may be desirable to deliver the therapeutic neurotoxin fragment via a catheter, or aerosolizer or inhaler, and the energy via a catheter placed in the vicinity of the targeted cell.

In a further aspect of the invention, it may be desirable to deliver the therapeutic neurotoxin fragment and the membrane transport energy via an implantable generator and drug delivery pump.

In a further aspect of the invention, it may be desirable to deliver the therapeutic neurotoxin fragment via a catheter, or aerosolizer (nebulizer) or inhaler, and the energy via an external energy source adapted to target the applied energy in the vicinity of the targeted cell.

In other aspects, embodiments of the present invention provide treatments for any disease or condition for which rhinorrhea is a result or symptom.

Rhinorrhea is the term describing the effluence of mucus from the lining of the nasal passages, nasopharynx, or paranasal sinuses. Rhinorrhea can be a symptom of a number of diseases such as the common cold, sinusitis or rhinitis, Rhinitis (inflammation of the airways) falls into two major categories—allergic and non-allergic (or vasomotor) rhinitis. Each can have several subcategories. Sinusitis is an infection or inflammation of the paranasal sinuses. Sinusitis may have a number of different causes, and can be the result of chronic inflammation of the nasal passages, for example as a result of chronic rhinitis.

Allergic rhinitis is an immunologic response modulated by IgE and characterized predominantly by sneezing, rhinorrhea, nasal congestion, and pruritus of the nose. It may be seasonal (a condition commonly referred to as hay fever) or perennial. The seasonal form is caused by allergens released during tree, grass, or weed pollination, whereas the perennial form is caused by allergies to animal dander, dust mites, or mold spores with or without associated pollinosis. Data also suggest that urban air pollutants from automobiles and other sources may have an adjunctive effect.

Nonallergic rhinitis is a diagnosis of rhinitis without any immunoglobulin E (IgE) mediation, as documented by allergen skin testing. Hence, the rhinorrhea, sneezing, pruritus, and congestion do not result from allergy or hypersensitivity and continue to persist, whether continuously or sporadically. Nonallergic rhinitis affects 5-10% of the population. Nonallergic rhinitis has 7 basic subclassifications, including infectious rhinitis, nonallergic rhinitis with eosinophilia syndrome (NARES), occupational rhinitis, hormonal rhinitis, drug-induced rhinitis, gustatory rhinitis, and vasomotor rhinitis. Patients may or may not present with the same symptoms seen in allergic rhinitis.

According to the present invention, botulinum toxin, ricin, exotoxin A, diphtheria toxin, cholera toxin, tetanus toxin, other neurotoxins, and active fragments thereof are delivered to a patient's nasal membrane while applying energy to target cells within the membrane under conditions which cause a reversible (or in some instances non-reversible) poration of the cell membranes to enhance delivery of the toxin into the cells. The region where the toxin is introduced may comprise any portion of the nasal cavity, such as a single paranasal sinus or portion thereof, a main nasal passage, two or more paranasal sinuses, or in some cases may comprise substantially the entire nasal cavity of the patient. A particular target region for the toxin may comprise the nasopharynx which is at the back of the nasal passage. The nasopharynx comprises a cluster of goblet cells which are responsible for mucus secretion and which are susceptible to the disabling mechanism of the botulinum toxin and other neurotoxins.

The energy is preferably selectively applied to a targeted region containing a variety of cell types, including goblet cells, epithelial cells, ciliated and non-ciliated columnar cells, basal cells, and less or no energy applied to untargeted regions. It will be appreciated that the energy may be applied to regions of the nasal membrane which are the same or different from the regions to which the toxin has been introduced. By controlling the delivery area of both the toxin delivery and the energy delivery, the methods and apparatus of the present invention can more specifically target the epithelial or goblet and other recipient cells of interest while minimizing the amount of toxin which enters non-targeted cells. That is, only those cells in the nasal membrane which are exposed to both the toxin and the applied energy will preferentially be permeablized or porated to receive the toxin within the cytoplasm of the cell.

The toxin to be delivered may comprise any neurotoxin capable of disabling mucus secretion in epithelial or goblet cells and other mucus-producing nasal cells. Preferably, the toxin comprises botulinum toxin, although other toxins such as ricin, exotoxin A, diphtheria toxin, cholera toxin, tetanus toxin, other neurotoxins, and active fragments thereof may also find use. In preferred aspects of the present invention, only an active fragment of the toxin will be delivered to the nasal cavity. botulinum toxin and the other toxins listed above commonly comprise both a heavy chain and a light chain. The heavy chain is responsible for binding to the target cells and mediating passage of the light chain into the cytoplasm of the target cells. By delivering only the light or active chain of these toxins (after removal of the heavy chain or recombinant production of only the light chain), the risk of accidental delivery of the toxin to non-target cells is greatly reduced. Delivery of the active or light chain fragments into the target cells, according to the present invention, is mediated and enhanced by the selective application of an energy which porates the cell membrane to allow entry of the light chain or active fragment. The presently preferred botulinum light chain fragment may be derived from any one of the seven presently known botulinum types A-G.

Any type of energy which is capable of reversibly permeablizing or porating the cell wall to allow passage of the toxin molecule, either whole toxin or preferably light chain fragment, into the cell cytoplasm may be applied to the cell membrane. Thus, energy may comprise various forms of electrical pulses, acoustic pulses, X-ray energy, microwave energy, or the like, and combinations thereof. Preferably, the energy will be either pulsed electrical energy of the type which is commonly used for cellular electroporation or will be ultrasonic energy of the type commonly employed for sonoporation of cells. The energy may be applied using the same catheters or other structures which are used for delivering the toxins. Alternatively, the energy may be applied using separate external or internal sources, such as using separate external ultrasonic transducers and/or ultrasound wave guides capable of delivering focused or unfocused ultrasound into the target tissues of the nasal cavity.

In specific embodiments of the methods of the present invention, the toxin may be introduced to the target region through a catheter. For example, the catheter may carry a balloon which engages the nasal membrane in order to effect delivery of the toxin to the target cells. In a particular example, the balloon is porous over at least a portion of its area so that the toxin may be released to specific areas of the nasal membrane, typically being incorporated into a suitable liquid, gel, or other fluid or fluidizable carrier. In other embodiments, the toxin may be introduced through one or more needles carried on the catheter, and in still other embodiments the toxin may be aerosolized from a small port, nozzle, or other orifice or structure on the catheter.

While the energy may be applied from a separate external source, as generally described above, the energy will most often be applied from the same catheter or other apparatus used to deliver the toxin. For example, when ultrasonic or other acoustic energy is being applied, the transducer may be on or associated with the catheter. In a particular example, it is shown that the transducer may be located within or beneath the porous balloon which is used to deliver toxin to the nasal membrane. When electrical energy is used for poration, the electrodes may be on the catheter within or surrounding the region which delivers the energy to the nasal membrane. In other instances, the energy may be applied from a separate catheter or other device adapted for intranasal introduction. In still other instances, the energy application will apply energy transcutaneously, for example from the skin of the face, typically surrounding the nose over the sinus cavities.

In addition to the methods described above, the present invention further provides systems for delivering toxins to goblet and other target cells as defined above in a nasal membrane. The systems may typically comprise a catheter adapted to introduce a toxin to a region adjacent to the target cells. An energy applicator is further provided for applying energy to the target cells under conditions which cause a reversible poration of the cell membranes to enhance delivery of the toxin. Systems may still further comprise a source of the toxin suitable for introduction from or through the catheter. The energy applicator may be mounted on or incorporated within the catheter, or may be a separate or intrabronchial external source. In an exemplary embodiment illustrated below, an external applicator may comprise a mask or other structure which fits over the nose and/or sinus region of the patient and which is capable of delivering acoustic to the target cells within the target regions.

When the energy applicator is incorporated with or within the catheter, the delivery pattern of the energy will usually be at least partially overlapping with the toxin delivery pattern of the catheter. For example, when a porous balloon is used for toxin delivery, the acoustic transducer, electroporation electrodes, or the like, will usually be disposed to deliver energy which at least partly overlaps with the dispersion pattern of the toxin. In some instances, the region of applied energy will be coextensive with the region of toxin dispersion. In other instances, the two regions will only partially overlap. In the latter case, the delivery of the toxin will be enabled or enhanced principally within the regions of overlap.

BRIEF DESCRIPTION OF THE DRAWINGS

Further features of the invention, its nature and various advantages will be more apparent from the accompanying drawings and the following detailed description, in which.

DETAILED DESCRIPTION OF THE INVENTION

The present invention is directed to methods and apparatus for targeting the non toxic delivery of a fragment of a neurotoxin, while still maintaining the catalytic or toxic effect of the neurotoxin fragment once it is non-toxically delivered to its targeted cell. For purposes of this specification, the term "non-toxic", "non-toxically" and the like refer to the state of the fragment molecule prior to delivery to a target location. In this description, the fragment neurotoxin is intended to retain its toxic effect once delivered to its catalytic environment; the intracellular matrix or cytosol of the targeted cell.

Devices and methods of the present invention may be directed to suitable "targeted regions" such as muscle cells in various regions of the body related to the various "therapeutic target conditions" or syndromes to be treated, as detailed in this specification above. Some particular examples include targeting mucosal and muscular lining of the lung, cholinergic cells in the region of tumors, myofacial regions, vascular smooth muscle cells, musculoskeletal regions and the like.

According to the present invention, energy fields (EF) may be applied to target regions in conjunction with the delivery of a fragmented neurotoxin such as BoNT-LC to facilitate the transfer of the neurotoxin fragment into the targeted cell, non-toxically via in vivo target cell permeabilization.

Use of Isolated Light Chain of Botulinum Neurotoxins

Figure 1:
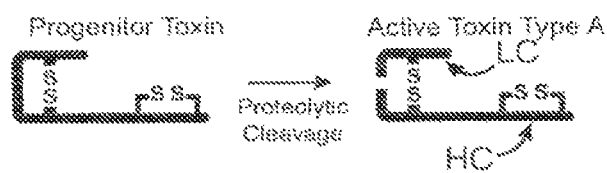
FIG. 1—depicts a schematic of the creation of neurotoxin Botulinum Toxin Type A (BoNT/A), including the light chain (LC) fragment or portion.

Generally, the BoNT molecule is synthesized as a single polypeptide chain of 150 kD molecular weight. The neurotoxin is then exposed to enzymes, either during cultivation of the *Clostridium botulinum* organism or subsequent to purification of the toxin, wherein specific peptide bonds are cleaved or "nicked" resulting in the formation of a dichain molecule referred to as BoNT. As shown in FIG. 1, dichain neurotoxin is composed of a light chain (LC) region 50 kD molecular weight linked by disulfide bonds to a heavy chain (HC) 100 kD molecular weight (Kistner, A., Habermann, E. (1992) *Naunyn Schmiedebergs Arch. Pharmacol.* 345, 227-334). When the light chain is separated from the heavy chains of botulinum toxin, neither chain is capable of blocking neurotransmitter release, however, the light chain alone is capable of blocking acetylcholine release if transported directly into the cell cytosol. (Ahnert-Hilger, G., Bader, M. F., Bhakdi, S., Gratzl, M. (1989) *J. Neurochem.* 52, 1751-1758 and Simpson, L. L. (1981) *Pharmacol. Rev.* 33, 155-188.) Focusing on the light chain, the isolation or separation process essentially renders the light chain "non-toxic" in a general environment, while still maintaining its effect or toxicity, once it is transported through the target cell membrane.

Over the past several years, the separation and purification of the light chain and heavy chain of BoNT has seen significant development activity. In the case of the heavy chain (HC), researchers are interested in its ability to bond with a target cell and deliver certain molecules into that cell. For example, various drug delivery applications have been suggested, for example, using the HC to bind to tPA so that a patient could inhale the HC bound tPA allowing it to cross the membrane of the lungs and be transported into the bloodstream for anticoagulation. Of particular interest to the present invention are the efforts to isolate and purify the light chain (LC) of the botulinum molecule. In its isolated and purified form, all HC elements are removed, rendering the LC incapable of crossing the cell membrane without assistance. Thus, the LC is non-toxic until delivered to the target cell cytosol by the delivery protocols of the present invention.

Various groups have been active in the area of isolation and purification. For example, companies such as Metabiologics, a group affiliated with the University of Wisconsin, the Center for Applied Microbiology and Research (CAMR), a division of the UK Health Protection Agency, List Biological Laboratories, Inc. of California, and other research groups throughout the world. Many of these companies provide purified preparations of botulinum neurotoxins from *Clostridium botulinum* types A and B. List Laboratories in particular provides recombinantly produced light chains from both types A, B, C, D and E.

According to the present invention, the therapeutic use and delivery of the light chain only may significantly improve the safety profile of certain applications of therapies utilizing BoNT. BoNT are some of the most lethal toxins known to man. All concerns about migration of the neurotoxin into unintended regions, and harm or toxicity to the patient or physician are eliminated by storing, handling, injecting and metabolizing the light chain only. In the absence of a specific membrane binding technology, the LC is completely non-toxic. In certain applications, such as the treatment of asthma, this is of critical import. In using BoNT to treat asthma, a large quantity of the purified LC substance may be introduced directly into the lung, and then specifically transported to target cells in the exact location and only during the period of use of application of the membrane transport technology, such as cell membrane permeabilization by energy. Once the membrane transport technology has been removed, turned off or otherwise inactivated, the remaining LC which has not been transported into target cells can simply be removed from the body by standard biologic processes for expelling foreign materials, e.g. coughing, immune system or lymphatic system transport and the like.

In addition, therapeutic use of only the LC of the neurotoxin BoNT may reduce the likelihood of the body developing an immunogenic response to the therapy that is seen with delivery of the intact toxin. This could be a major advantage in light of the repetitive application or injection of the toxin that is required to maintain a therapeutic effect.

Non-Toxic Membrane Transport Mechanisms

To date, the main application of purified or isolated light chain has been the study of its mechanism of action. To further this research, literature has reported the use of certain detergent based permeabilization techniques to deliver fragment BoNT (Bittner M A, DasGupta B R, Holz R W. Isolated light chains of botulinum neurotoxins inhibit exocytosis. Studies in digitonin-permeabilized chromaffin cells. J Biol Chem 1989 Jun. 25; 264(18):10354-10360.) Further reference to the mechanism of permeability of cell membranes to deliver botulinum toxin are mentioned in U.S. Pat. No. 6,063,768 to First, and U.S. Pat. No. 6,632,440 to Quinn, Chaddock, et al "Expression and Purification of Catalytically Active Non-Toxic Endopeptidase Derivatives of *Clostridium botulinum* toxin type A", *Protein Expression and Purification*, 25 (2002) 219-228, contemplating the insertion of the light chain of BoNT into a target cell without the heavy chain for purposes of deriving vaccines or in bench top studies of cell mechanisms of action. The contents of these references are expressly incorporated by reference in their entirety. None of the teachings contemplate a delivery of a fragment of neurotoxin using a clinically acceptable permeabilization technique in vivo for therapeutic uses as is contemplated by the present invention.

For purposes of this specification, the term "poration" includes various forms of electroporation, such as the use of pulsed electric fields (PEFs), nanosecond pulsed electric fields (nsPEFs), ionophoreseis, electrophoresis, electropermeabilization, as well as other energy mediated permeabilization, including sonoporation (mediated by ultrasonic or other acoustic energy), and/or combinations thereof, to create temporary pores in a targeted cell membrane. Similarly, the term "electrode" or "energy source" used herein, encompasses the use of various types of energy producing devices, including x-ray, radiofrequency (RF), DC current, AC current, microwave, ultrasound, adapted and applied in ranges to produce membrane permeabilization in the targeted cell.

Reversible electroporation, first observed in the early 1970's, has been used extensively in medicine and biology to transfer chemicals, drugs, genes and other molecules into targeted cells for a variety of purposes such as electrochemotherapy, gene transfer, transdermal drug delivery, vaccines, and the like.

In general, electroporation may be achieved utilizing a device adapted to activate an electrode set or series of electrodes to produce an electric field. Such a field can be generated in a bipolar or monopolar electrode configuration. When applied to cells, depending on the duration and strength of the applied pulses, this field operates to increase the permeabilization of the cell membrane and reversibly open the cell membrane for a short period of time by causing pores to form in the cell lipid bilayer allowing entry of various therapeutic elements or molecules, after which, when energy application ceases, the pores spontaneously close without killing the cell after a certain time delay. As characterized by Weaver, *Electroporation: A General Phenomenon for Manipulating Cells and Tissues* Journal of Cellular Biochemistry, 51:426-435 (1993), short (1-100 .mu.s) and longer (1-10 ms) pulses have induced electroporation in a variety of cell types. In a single cell model, most cells will exhibit electroporation in the range of 1-1.5V applied across the cell (membrane potential).

In addition, it is known in the art that macromolecules can be made to cross reversibly created pores at voltages of 120V or less applied to cells for durations of 20 microseconds to many milliseconds. For applications of electroporation to cell volumes, ranges of 10 V/cm to 10,000 V/cm and pulse durations ranging from 1 nanosecond to 0.1 seconds can be applied. In one example, a relatively narrow (pee) high voltage (200V) pulse can be followed by a longer (>msec) lower voltage pulse (<100V). The first pulse or series of pulses open the pores and the second pulse or series of pulses assist in the movement of the BoNT-LC across the cell membrane and into the cell.

Certain factors affect how a delivered electric field will affect a targeted cell, including cell size, cell shape, cell orientation with respect to the applied electric field, cell temperature, distance between cells (cell-cell separation), cell type, tissue heterogeneity, properties of the cellular membrane and the like.

Various waveforms or shapes of pulses may be applied to achieve electroporation, including sinusoidal AC pulses, DC pulses, square wave pulses, exponentially decaying waveforms or other pulse shapes such as combined AC/DC pulses, or DC shifted RF signals such as those described by Chang in *Cell Potation and Cell Fusion using and Oscillating Electric Field,* Biophysical Journal October 1989, Volume 56 pgs 641-652, depending on the pulse generator used or the effect desired. The parameters of applied energy may be varied, including all or some of the following: waveform shape, amplitude, pulse duration, interval between pulses, number of pulses, combination of waveforms and the like.

There are at least two general power categories of medical ultrasound waves. One category of medical ultrasound wave is high acoustic pressure ultrasound. Another category of medical ultrasound wave is low acoustic pressure ultrasound.

Acoustic power is expressed in a variety of ways by those skilled in the art. One method of estimating the acoustic power of an acoustic wave on tissue is the Mechanical Index. The Mechanical Index (MI) is a standard measure of the acoustic output in an ultrasound system.

High acoustic pressure ultrasound systems generally have a MI greater than 10. Low acoustic pressure systems generally have a MI lower than 5. For example, diagnostic ultrasound systems are limited by law to a Mechanical Index not to exceed 1.9.

Another measurement used by those skilled in the art is the spatial peak, peak average intensity (Isppa). The intensity of an ultrasound beam is greater at the center of its cross section than at the periphery. Similarly, the intensity varies over a given pulse of ultrasound energy. Isppa is measured at the location where intensity is maximum averaged over the pulse duration. Isppa for high acoustic pressure or high intensity focused ultrasound (HIFU) applications ranges from approximately 1500 W/cm2. to 9000 W/cm2. Diagnostic ultrasound equipment, for instance, will generally have, and an Isppa less than 700 W/cm2.

Yet another way in which ultrasound waves can be characterized is by the amplitude of their peak negative pressure. High acoustic pressure or HIFU applications employ waves with peak amplitudes in excess of 10 MPa. Low acoustic pressure ultrasound will generally have peak negative pressures in the range of 0.01 to 5.0 MPa. Diagnostic ultrasound equipment, for example, will generally have a peak amplitude less than 3.0 MPa.

Both high and low acoustic pressure ultrasound systems generally operate within the frequency range of 20 KHz-10.0 MHz Interventional applications (such as in blood vessels) operate clinically up to about 50 MHz. Also opthalmologic applications up to about 15 MHz. Diagnostic imaging typically uses frequencies of about 3 to about 10 MHz. Physical therapy ultrasound systems generally operate at frequencies of either 1.0 MHz or 3.3 MHz.

High acoustic pressure ultrasound or high intensity focused ultrasound has been used for tissue disruption, for example for direct tumor destruction. High intensity focused ultrasound using high acoustic pressure ultrasound is most commonly focused at a point in order to concentrate the energy from the generated acoustic waves in a relatively small focus of tissue.

Systems for permeabilization of target tissue cell membranes may employ either high acoustic pressure or low acoustic pressure ultrasound. Some embodiments may preferably employ relatively low acoustic pressure, for example the systems described herein where the transducers are mounted on the delivery devices and operate inside the body. Other systems may operate at interim acoustic pressure ranges. For example, systems described herein which employ an external ultrasound generator and transducer and which conduct the ultrasound to the target tissues through the use of a wave guide. In these systems, losses due to transduction through the wave guide can be compensated for by increasing the input power to the wave guide until adequate power is delivered to the target tissue. Finally, some systems described herein may employ focused or partially focused higher pressure ultrasound, for example the systems which employ an external mask to conduct the ultrasonic power through the tissues to the target tissues. It should be appreciated that combinations of high and low acoustic pressure systems may also be employed.

Figure 2A:
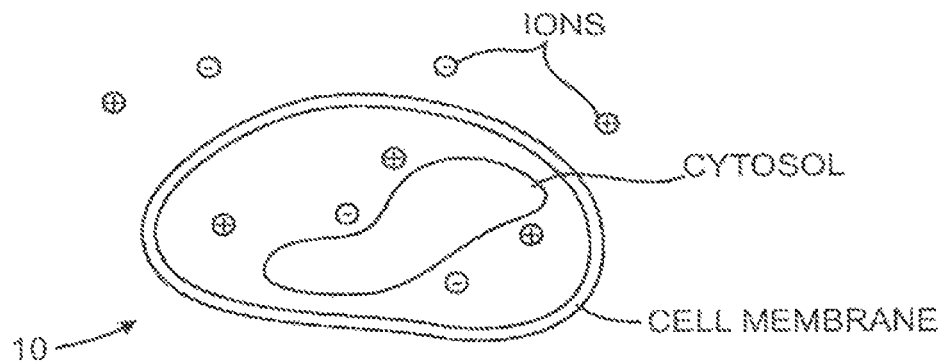
FIG. 2A—depicts a schematic of a target cell, including the cell membrane, and inner cellular matrices.
Figure 2B:
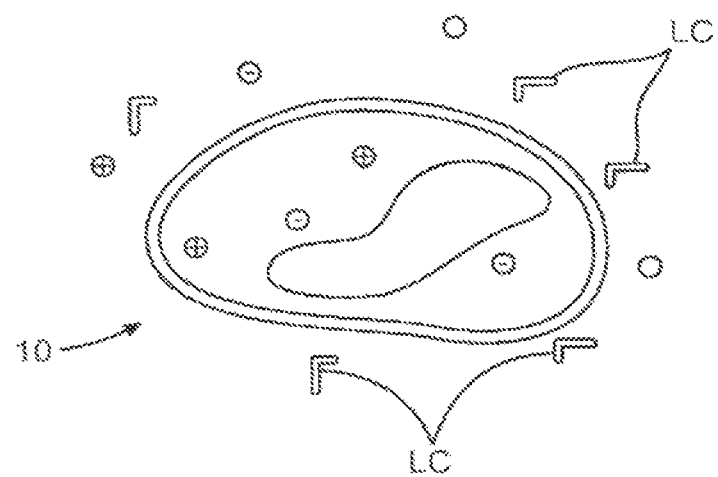
FIG. 2B—depicts a schematic of the target cell wherein LC molecule has been introduced.
Figure 3A:
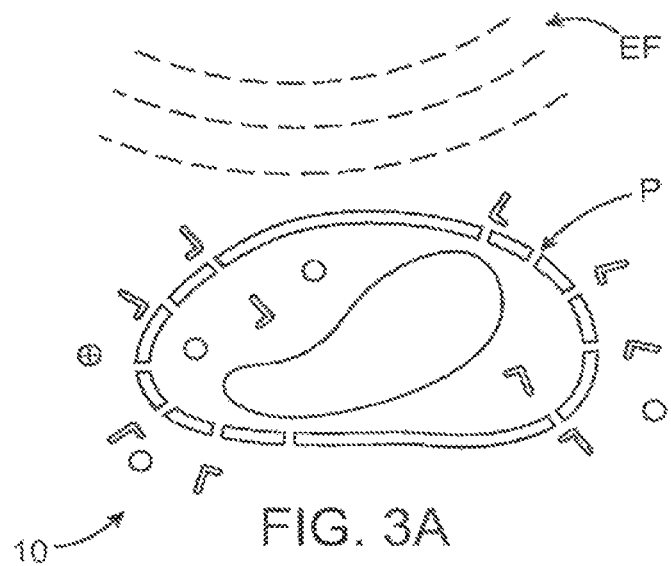
FIG. 3A-3B—depicts a the target cell of FIG. 2 showing application of an energy field (EF) to produce permeabilization or pores (P) in the cell membrane, and introduction of the LC fragment therethrough.
Figure 3B:
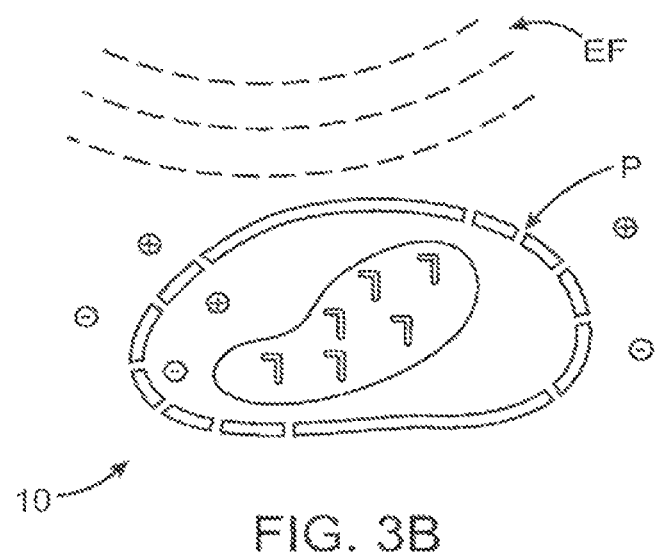
Figure 4:
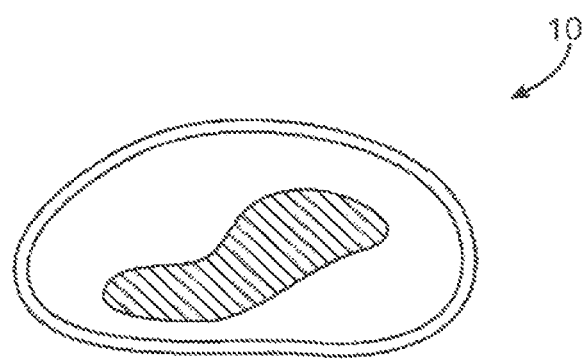
FIG. 4—depicts a schematic of a cell wherein the energy field has been discontinued, and neurotransmission of the cell has been effectively blocked.

A schematic example of the methods of the present invention are shown in FIGS. 2-4 in a simplified single cell model. A targeted cell 10, e.g. a goblet cell of the type which line the nasal cavity membrane, is shown in FIG. 2A. Fragmented neurotoxin such as BoNT-LC (LC) is introduced into the vicinity of the targeted cell as depicted in FIG. 2B. An energy field (EF) is applied in accordance with the present invention resulting in the transfer of the BoNT-LC through pores P to the intracellular matrix (cytosol) as shown in FIGS. 3A and 3B. Once this transfer has occurred, the release of neurotransmitters of the target cell are then blocked or disrupted, and once energy application is discontinued, the pores P in the cell membrane recover or close as depicted in FIG. 4.

Of particular interest for application in certain therapeutic target conditions is the developing field of sonoporation, and the terms "poration" and "permeablization" will also cover forms of cellular sonoporation. Just as pulses of high voltage electricity can open transient pores in the cell membrane, ultrasonic energy can do the same. See for example Guzman et al. "Equilibrium Loading of Cells with Macromolecules by Ultrasound: Effects of Molecular Sizing and Acoustic Energy," Journal of Pharmaceutical Sciences, 91:7, 1693-1701, which examines the viability of ultrasound to deliver molecules of a variety of sizes into target cells. In addition, techniques for nebulizing fluids and aqueous drugs are well known in the art, and as such, devices of the present invention may be adapted to introduce a BoNT-LC solution to a target region, such as the lung or the nasal passage and then effect selective membrane transport of the BoNT-LC into the cell using sonoporation.

For example, U.S. Pat. No. 6,601,581 to Babaev, hereby incorporated by reference in its entirety, describes certain techniques for delivering therapeutic agents using ultrasound for pulmonary delivery via an aerosolizing technique. Further, Guzman, et al, depicts delivery of molecules from a low of 62 Da up to 464 kDa (a range of 0.6-18.5 nm radius). Since the LC of the botulinum toxin is in the 50 kDa range, the LC would be very susceptible to sonoporetic delivery. Furthermore, Guzman, et al also showed that for all size ranges tested, levels of macromolecule within the cell reached thermodynamic equilibrium with the extracellular environment, and the cell uptake also depended on the energy delivered, as expressed in J/cm2. As such, the sonoporetic delivery of LC to the targeted regions may be controlled by adjusting the concentration of the LC exposed to the target region (e.g. wall or membrane of the lung), the energy delivered to the target region, or both.

Catheter Devices

To achieve the goals of the present invention, it may be desirable to employ methods and apparatus for achieving cell membrane permeabilization via the application of an energy source, either from a catheter located directly in the vicinity of the targeted cells, or an externally focused energy system. For purposes of this specification, the term "catheter" may be used to refer to an elongate element, hollow or solid, flexible or rigid and capable of percutaneous introduction to a body (either by itself, or through a separately created incision or puncture), such as a sheath, a trocar, a needle, a lead. Further descriptions of certain electroporation catheters are described in U.S. Patent Application 60/701,747, filed on Jul. 22, 2005, the full disclosure of which is expressly incorporated herein by reference.

Figure 5:
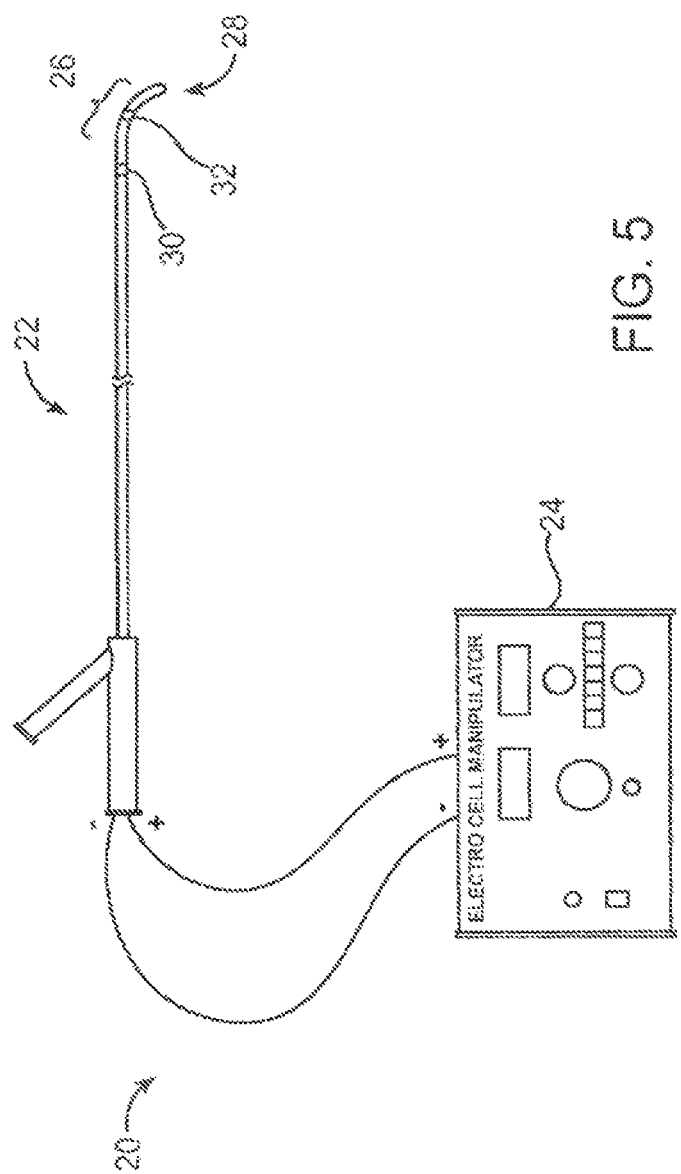
FIGS. 5, 5A-5B—depicts various embodiments of a delivery device of the present invention utilizing multiple energy transmission elements and an energy transmission system.
Figure 5A:
Figure 5B:

FIGS. 5 and 5A-5B depict a system 20 utilizing an electroporation catheter 22 for selective electroporation of targeted cells. In certain configurations of the present invention, voltages may be applied via the electroporation catheter 22 to induce reversible electroporation at the same time as the catheter delivers the fragmented neurotoxin to the targeted region.

Referring to FIG. 5, electroporation catheter system 20 further comprises a pulse generator 24 such as those generators available from Cytopulse Sciences, Inc. (Columbia, Md.) or the Gene Pulser Xcell (Bio-Rad, Inc.), or IGEA (Carpi, Italy), electrically connected to a catheter having a proximal end and a distal end and adapted for minimally invasive insertion into the desired region of the body as described herein. The catheter further comprises an electroporation element 26 at a distal 28 end thereof. The electroporation element may include for example a first and second electrode 30 and 32 operatively connected to the pulse generator for delivering the desired number, duration, amplitude and frequency of pulses to affect the targeted cells. These parameters can be modified either by the system or the user, depending on the location of the catheter within the body (intervening tissues or structures), and the timing and duration of reversible cell poration desired.

Figure 6A:
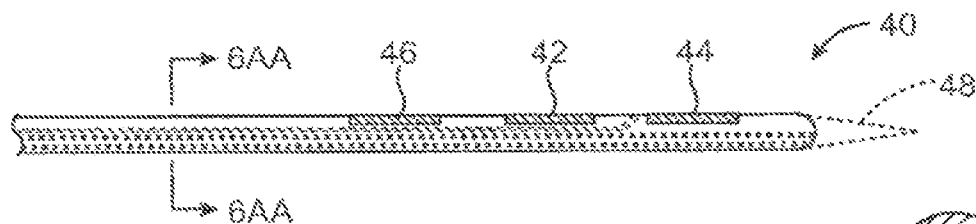
FIGS. 6A-D, 6AA, and 6CC—depict various electrode catheter configurations adapted to deliver energy or energy and therapeutic agents to target tissue.
Figure 6A:
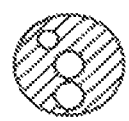

FIG. 5A depicts an arrangement of electrodes 30 and 32 that produces an electric field concentrated in a lateral direction from the catheter body whereas, FIG. 5B shows a device constructed to create a more uniform electric field about the shaft of the catheter body. Further catheter device and electrode configurations are shown in FIGS. 6A-6D. FIG. 6A depicts an elongate catheter 40 having first and second electrodes 42 and 44 near the distal tip thereof, and including a monitoring or stimulation electrode 46 in the vicinity of the active porating electrodes for localizing the treatment area. In some embodiments, the monitoring or stimulating function may be performed by one or more of the treatment electrodes. The catheter device may have an optional sharp tip 48 to facilitate percutaneous introduction. Cross-sectional view FIG. 6A A shows various lumens provided for neurotoxin fragment delivery and other purposes.

Figure 6B:
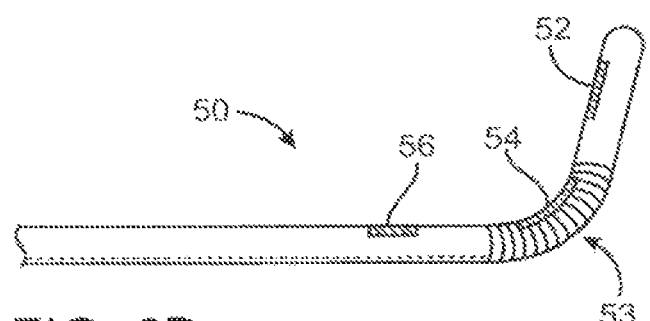

FIG. 6B is a similar catheter device 50 having electrodes 52, 54, and 56, but is further adapted to be steerable, or articulate at a region 53 near the distal end of the device, e.g., including a pull wire for deflecting the tip. Such steering ability enables the operator to introduce the device into tight or tortuous spaces (such as the bronchial passages or cardiovascular vessels) so that optimal placement of the device at the target location may be achieved.

Figure 6C:
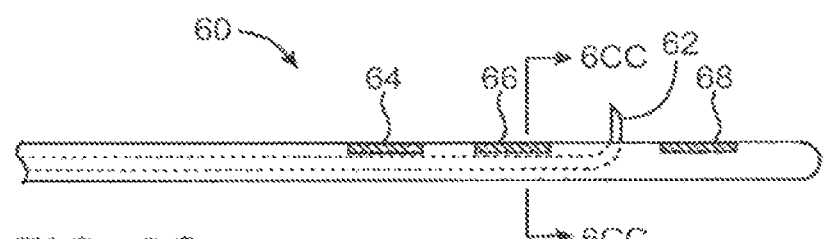
Figure 6C:
Figure 10:
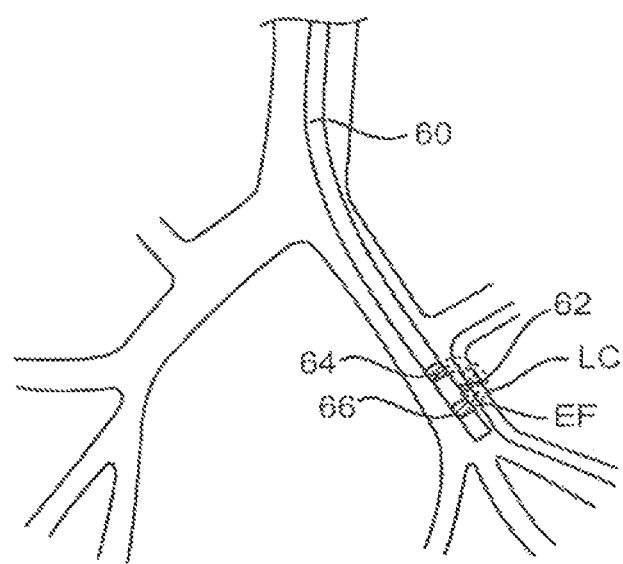
FIG. 10—depicts an interstitial method of use of the present invention.

FIG. 6C depicts a catheter device 60 having a needle 62 or other injection element to allow for the injection of a therapeutic agent such as a fragmented neurotoxin before, during or after the application of the pulsed energy or electroporation. The catheter 60 further includes electrodes 64 and 66 or other poration components as discussed herein. The injection element may be a needle 62 as shown in FIG. 6C, an infusion port, or other infusion means. Needle 62 may also be used as an electrode in addition to an injection port. Electrode 68 comprises a monitoring or stimulating electrode. FIG. 10 depicts the use of a catheter of FIG. 6C to treat bronchial tissue in the lung for a variety of respiratory ailments such as asthma. FIG. 6CC is a cross-sectional view taken along line 6CC-6CC in FIG. 6, showing a co-axial sleeve design.

Figure 6D:
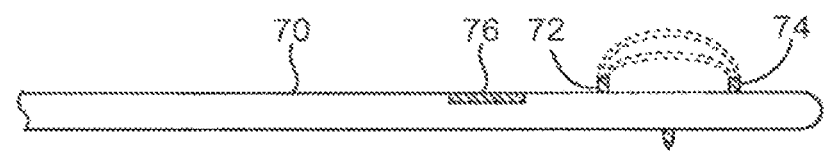

FIG. 6D depicts a catheter device 70 having electrode elements 72 and 74 that are adapted to extend laterally from the main catheter body, and in some cases, penetrate the surrounding tissue prior to application of energy. In doing so the depth and direction of the energy field created by the electroporative process, may be further controlled. A monitoring/stimulating electrode 76 will usually also be provided. Elements 72 and 74 may also be used as injection ports for introduction of toxin or toxin fragments.

Figure 7:
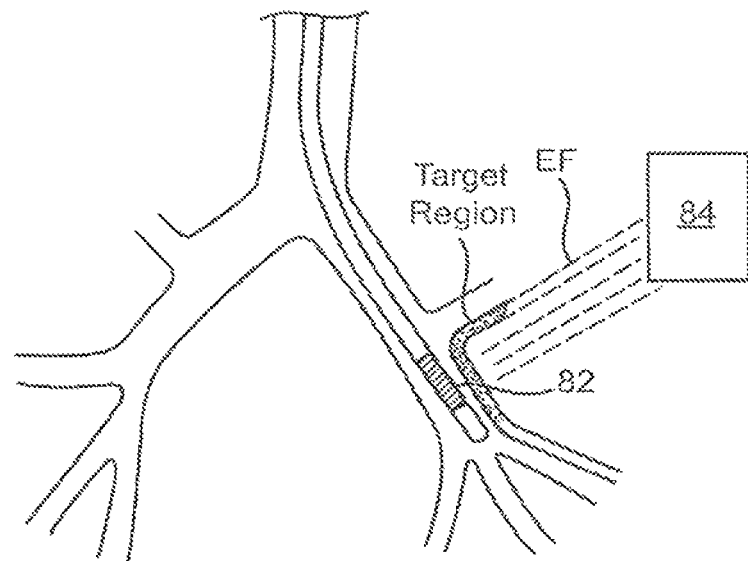
FIG. 7—depicts an alternative embodiment of the present invention wherein one of the multiple energy transmission elements is placed at the targeted cell site, and the other in a location remote therefrom.

FIG. 7 depicts the use of a catheter device 80 of the present invention for treatment of a respiratory tract, by positioning at least one electrode (82) at the target region, and a second electrode (84) remote from the target region, the target region being positioned between 82 and 84, such that activation of the electrodes produces an energy field (EF) therebetween, the size and intensity of which can be controlled by the placement of the electrodes relative to each other and the targeted region.

Figure 8:
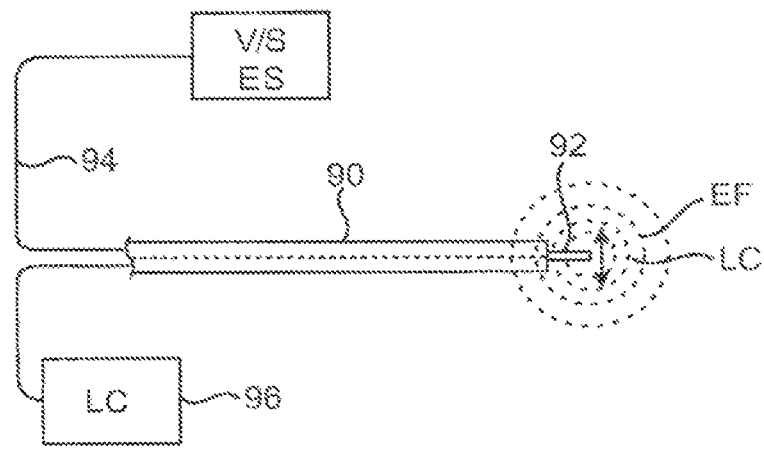
FIG. 8—depicts an embodiment of the present invention utilizing an ultrasound element on a catheter device.
Figure 11:
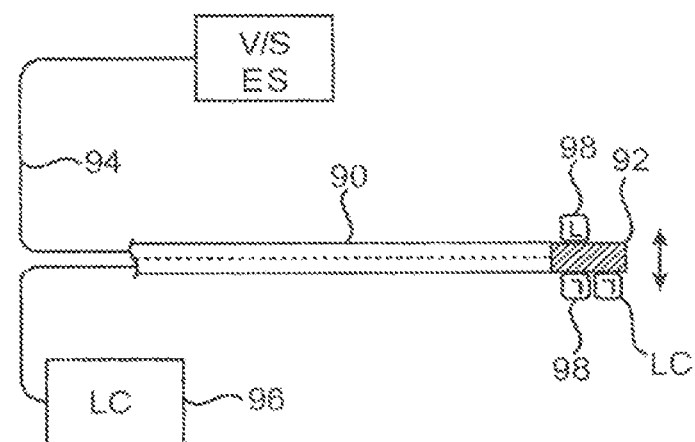
FIG. 11—depicts an embodiment of the present invention utilizing an aerosolizing element.

FIG. 8 depicts catheter 90 constructed in accordance with the principles of the present invention utilizing an ultrasonic element 92 that may be particularly useful in delivery of the BoNT-LC to bronchial tissue (lung) and/or nasal tissue that provides a broad but targeted transport of the LC across the target cell walls, for example, epithelial and goblet cell walls. In this device, ultrasound energy is delivered to the distal end of the catheter device via an ultrasonic waveguide 94 that is operatively connected to an ultrasound energy source (U/SES). The LC fragment would be delivered from a receptacle 96 via the same lumen as the waveguide via a lumen provided the distal tip of the device. In operation, the ultrasonic energy would cause the LC solution to be nebulized, forming a mist or aerosol 98 within the lung, as shown in FIG. 11. The aerosol 98 itself, in the appropriate concentrations, may act as an ultrasound coupler, conveying the ultrasonic energy to the wall of the lung or other targeted cellular structures, causing sonoporation of the targeted cells whereby the LC fragment is transmitted across the cell membranes to become an effective neurotransmitter blocker. In an alternative embodiment, an ultrasonic transducer may be located directly at the tip of the delivery device, eliminating the need for a wave guide. Various catheters useful for delivering vibrational energy to tissue are described in U.S. Pat. Nos. 6,361,554 and 6,464,680 to Brisken, the contents of which are expressly incorporated herein by reference in their entirety, for various therapeutic effects, such as enhancing cellular absorption of a substance.

Since air is a very effective insulator against transmission of ultrasonic energy, the treatment area in the lung may be more precisely controlled by the concentration of the LC mist and the intensity of the ultrasonic energy. A fairly steep drop off in energy delivery would occur as mist concentration diffused, effectively protecting areas outside the predetermined radius surrounding the distal end of the delivery device. According to the present invention, since no functional neurotoxin exists without an effective membrane transport technology, terminating the energy application leaves a harmless mist that is then coughed up (if resident in the lungs) or otherwise metabolized and excreted by the body.

Any of the catheter devices described herein, or described in the contemporaneously filed U.S. Patent Application 60/701,747, previously incorporated by reference in its entirety, may be adapted to include an energy delivery element such as those described herein for purposes of providing a membrane transport system for delivery of a fragment of neurotoxin. In addition, certain catheter devices and methods such as those set forth in U.S. Pat. Nos. 5,964,223 and 6,526,976 to Baran may be adapted to include energy transmission elements capable of producing a porative effect at the cellular level, including electrodes, ultrasonic elements and the like, for treatment in the respiratory tract.

Furthermore, any of the foregoing systems may include electrodes or other monitoring systems either located on the treatment catheter, or external to the patient, to determine the degree of treatment to the region, including, thermocouple, ultrasound transducers, fiberoptics, sensing or stimulating electrodes. Further, it may be desirable to incorporate multiple pairs of electrodes that may be activated in pairs, in groups, or in a sequential manner in order to maximize the desired shape of the energy field (EF) while minimizing the field strength requirements.

Implantable Devices

Figure 12:
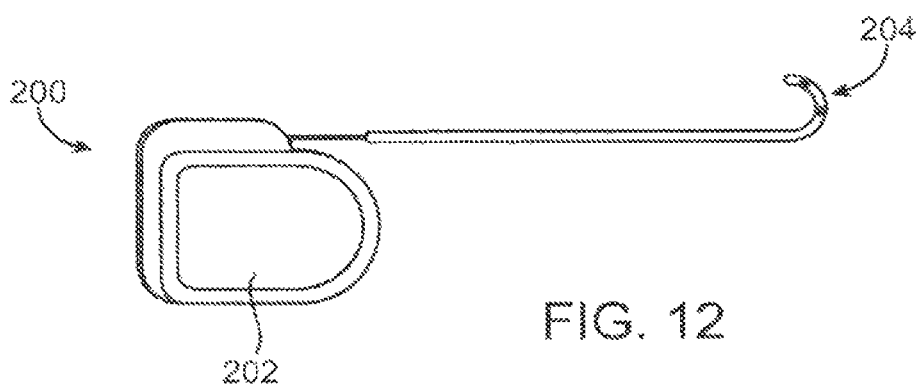
FIG. 12—depicts a fully implantable pulse generator, lead and agent delivery pump of the present invention.

Just as energy may be delivered to a targeted region to facilitate the delivery of fragmented neurotoxin via a catheter system, it is also within the scope of the present invention to deliver neurotoxins via an implantable system, including a pulse generator, lead and drug pump as depicted in FIG. 12. A neuromodulation system 200 may be fully implantable, having a pulse generator and a power supply or battery and be operatively connected to a programmable drug delivery pump all housed within a module 202, including a reservoir in which the BoNT-LC is stored for delivery over time using the principles of the present invention and technology of the programmable drug pump. A catheter 204 can be adapted to deliver the drug and poration energy to a desired target location in the patient's body.

Examples of useful implantable devices of the present invention are, devices such as those set forth in U.S. Pat. No. 5,820,589 to Torgerson et al, the entire contents of which are hereby incorporated by reference, the SynchroMed® programmable pump available from Medtronic, Inc. (Minneapolis, Minn.), and the neurostimulation units such as the RESTORE* or SynergyPlus® available from Medtronic, Inc., modified if necessary to deliver the desired voltage range for cell membrane permeabilization. Implantation of the neurostimulation device is further described in U.S. Pat. No. 6,847,849, incorporated herein by reference in its entirety.

The non-toxic nature of the BoNT in the absence of applied energy makes it possible to contemplate placing a bolus of neurotoxin in the body of a patient in what might otherwise be a toxic amount. This is particularly advantageous, since the traditional treatment regime using neurotoxins, is typically repeat injections of the toxins every 3 to 6 months and sometimes more frequently depending on the application. Certainly in more chronic conditions such as chronic pain, tremor, spasm, palsy and the like, such a fully implantable system may be highly desirable.

Non-Invasive Devices

Figure 13:
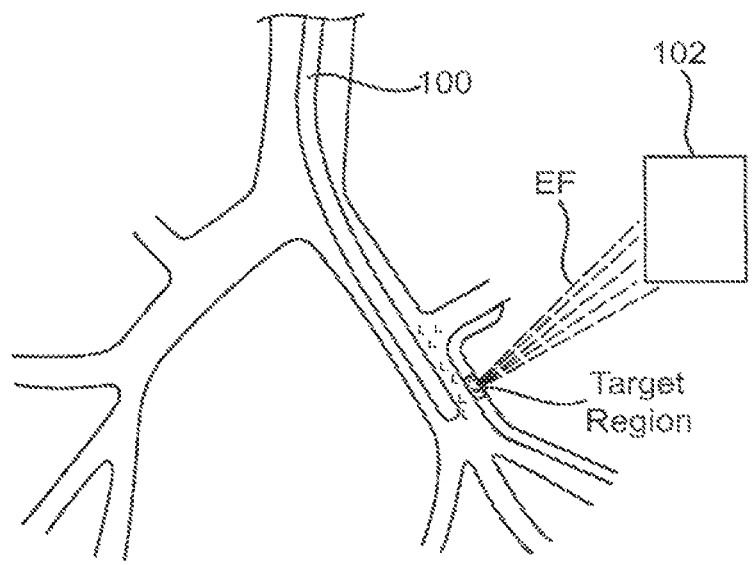
FIG. 13—depicts an embodiment of the present invention utilizing an external energy delivery source applied to the therapeutic agent applied in the vicinity of a targeted cell.
Figure 9:
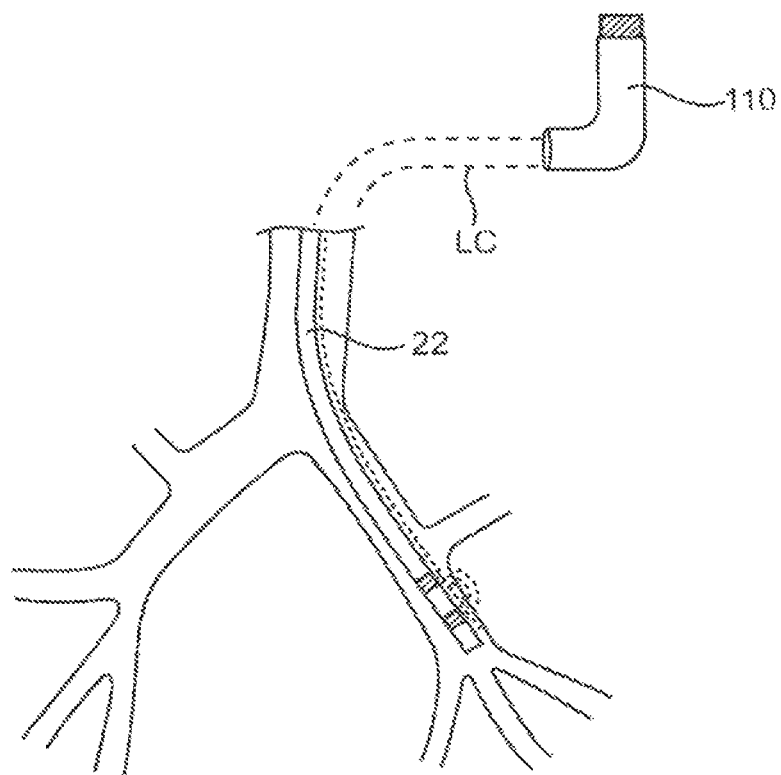
FIG. 9—depicts an embodiment of the present invention utilizing an inhaler with an in vivo energy delivery source.

It is within the scope of the invention to deliver either the energy or the therapeutic BoNT-LC non-invasively, or both. For example, FIG. 13 depicts delivery of the BoNT-LC via a catheter 100 placed in the bronchial passageway with the energy field (EF) delivered from outside the patient in the form of an energy system 102 such as focused ultrasound (HIFU), stereotactic x-ray beams, magnetic resonance transmission, and the like. As detailed in U.S. Pat. Nos. 6,626,855 and 6,719,694 to Weng, the contents of which are expressly incorporated herein by reference in their entirety, an ultrasound beam can be controlled from outside the patient to focus the ultrasound beam in the desired location and intensity. For use in the present invention, it may be desirable to pulse or otherwise attenuate the ultrasound beam to achieve reversible cellular poration at the targeted site. Further, due to its non-toxic state, the BoNT-LC may be inhaled by the patient using a standard inhaler device such as those using pressurized aerosols known as metered dose inhalers (MDI) available from Cardinal Health (Somerset, N.J.), the OPTIHALER® available from National Allergy Supply Incorporated (Georgia, USA), or a nebulizer breathing machine such as a Pari DURANEB 3000 portable nebulizer available from Medinfinity, Co. (Fountain Valley, Calif.). In addition, certain technology currently under development employing thermal aerosols, such as a the STACCATO™ vaporization technology from Alexza Molecular Delivery (Palo Alto, Calif.) may also be useful within the scope of the present invention. Such devices 110 may be used as depicted in FIG. 9 for treating a respiratory ailment such as asthma. Optionally, the drug can be delivered with the catheter 22 (as shown) or with the external sources of FIG. 13.

Figure 15:
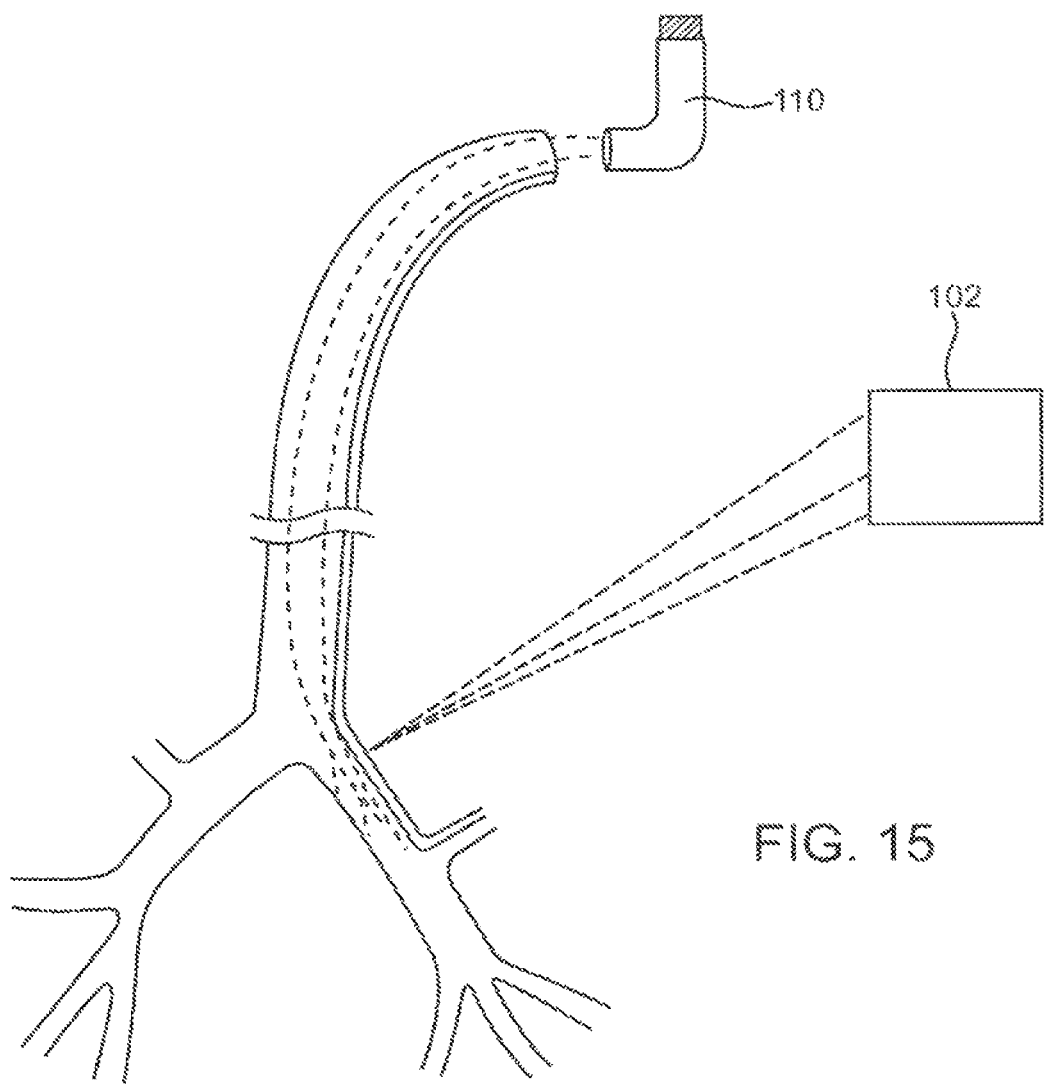
FIG. 15—depicts a method of use of a noninvasive agent delivery device coupled with a non-invasive energy source for treating a lumen or tract of the respiratory system.

A combination of these non-invasive approaches may also be advantageous as shown in FIG. 15, wherein an non-invasive inhaler 110 is used to deliver the BoNT-LC to the target region (such as the lung), and the energy is delivered to the target region by the non-invasive source 102 such as the focused ultrasound (HIFU), stereotactic x-ray, or magnetic resonance transmission as previously described. Due to its non-invasive technique, this approach may have broad appeal to a large patient population, including pediatric use, on an outpatient basis in a clinic designated for the treatment of specific respiratory ailments.

In a further aspect of the present invention, the fragmented molecule BoNT-LC may be delivered intravenously to a patient to achieve a systemic affect. A non-invasive energy application device, such as those described above, may then be targeted at the area of interest to porate the target area, thereby locally delivering the BoNT-LC to the region sufficiently porated by the applied energy.

Figure 14:
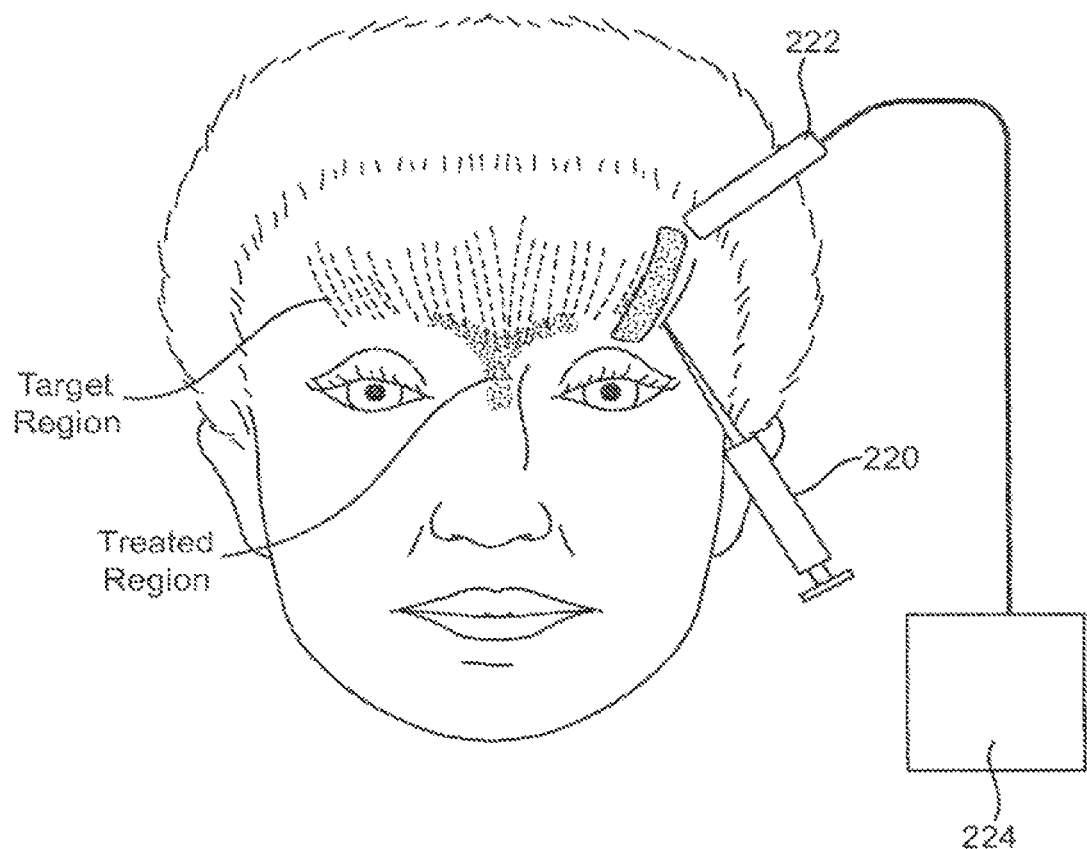
FIG. 14—depicts an embodiment of the present invention wherein the energy and therapeutic agent are delivered transdermally.

Cosmetic and Myofacial Applications. For some conditions, it may be desirable to apply the energy field from the surface of the skin to produce a porative effect, while injecting the BoNT-LC fragment into the targeted facial muscles as shown in FIG. 14. In operation, an injection device 220 places the BoNT-LC in the muscle to be treated (target region), and an energy transmission device such as an ultrasonic pen 222 with a single, or a series of ultrasonic elements located on the distal end and coupled to an energy transmission system 224, follows along the target region to controllably discharge the BoNT-LC fragments to the targeted cells leaving a highly controlled treated region. In some instances for treatments around the eye, it may be desirable to limit the penetration of the BoNT-LC to dermal or subdermal layers. In these applications, BoNT-LC may be applied transdermally with ultrasound assistance using techniques similar to those set forth in U.S. Pat. No. 4,767,402 to Kost the contents of which is expressly incorporated herein in its entirety or through transdermal electroporation.

Intraluminal Devices

It may further be advantageous to position catheters of the present invention through vessels in the body to direct them to various regions to affect neurotransmitters in the cardiovascular system. Intraluminal catheters such as those shown in United States Patent Applications 2001/0044596 to Jaafar and 2002/0198512 to Seward, hereby incorporated by reference in their entirety, may be used in this application of the present invention.

Treatment Enhancements

In some applications of the present invention, it may be desirable to assess the appropriate location for the therapy prior to treatment, the therapeutic effect as it is delivered, and ultimately the resulting effect. To achieve this, once the treatment device is in place adjacent the tissue to be treated, the energy generator may be activated, causing an energized field to be generated in the target area. Prior to activation of therapeutic voltages and agent, stimulation using one or more electrodes may be used to elicit a nerve response or reflex. By observing the nerve response, a target treatment location can be confirmed. Similarly, once the therapy has been delivered, a similar stimulation response may be sought, to determine presence or lack of neurogenic response.

In operation, effects of electroporation and delivery of a therapeutic dose of BoNT LC may be selective due to the cellular structure and orientation of the targeted cells. For example, targeted cells may be preferentially affected due to size, avoiding smaller or cross-oriented tissue cells.

In a further aspect of the present invention, the method of delivering the LC fragment of the BoNT molecule may include the use of a media that contains microspheres or microbubbles, such as Optison™ sold by GE Healthcare (www.amershamhealth-us.com/optison/). Delivery of an ultrasound energy (or other form of energy, for example, laser, RF, thermal, energy) to the media causes the microspheres to rupture, which causes a release of energy toward the targeted region. Such a technique may assist in the desired porative effect by reducing the amount of applied energy required to create poration in the targeted cell membrane. *Bioeffects Caused by Changes in Acoustic Cavitation Bubble Density and Cell Concentration: A Unified Explanation Based on Cell-to-Bubble Ratio and Blast Radius*, Guzman, et al. Ultrasound in Med. & Biol., Vol. 29, No. 8, pp. 1211-1222 (2003). In an alternative embodiment, the LC fragment may actually be contained or encapsulated within a microsphere to assist in delivery. Such enhancing elements may be delivered prior to energy application or during energy application.

In a further aspect of the present invention, it may be advantageous to heat the targeted cells or surrounding tissue by either applying thermal energy directly to the region, or directing a heated fluid, such as saline to the region through an injection element, to aid the cell poration process. Other substances may also be injected to aid in the transmission of the BoNT-LC into the intracellular membrane, such as amino acids, detergents or other agents that may facilitate the catalytic activity of the LC, in addition to the applied energy.

Figure 15A:
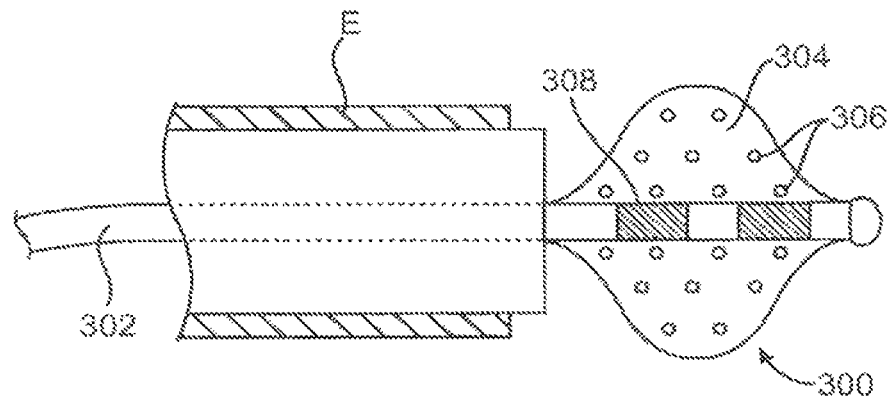
FIGS. 15A and 15B—depict use of a balloon for delivering toxin fragments in a lung.
Figure 15B:
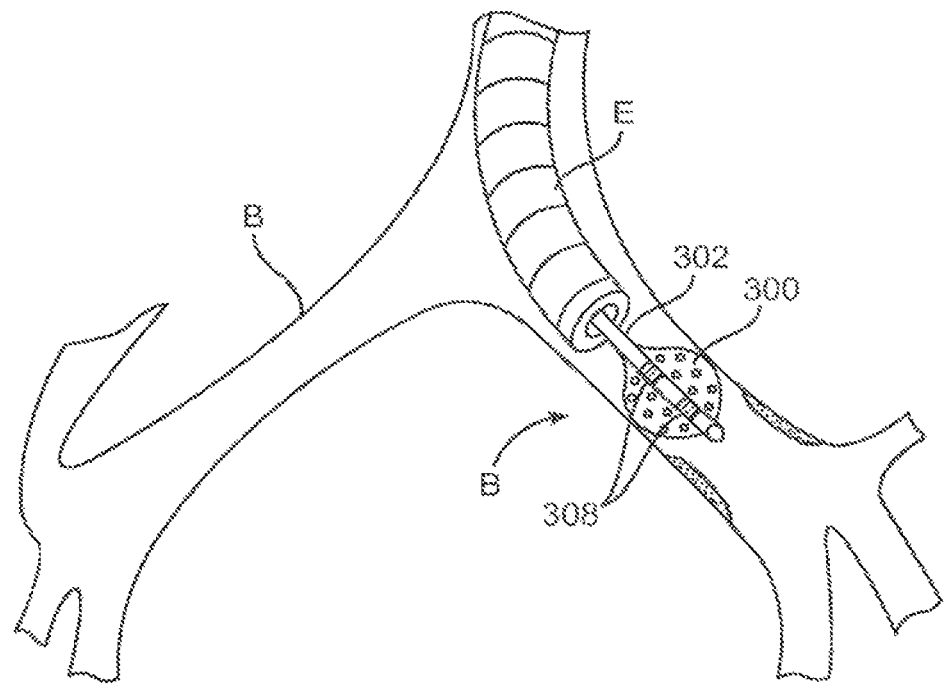

Referring now to FIGS. 15A and 15B, a balloon catheter 300 may be delivered to a target site in the bronchus B of a lung (FIG. 15B). Typically, the catheter 300 will be delivered through an endoscope E, and the shaft 302 of the catheter will comprise at least one lumen for inflating the balloon 304. The inflation medium may carry the toxin fragment which is released through ports 306 formed in the balloon itself. Thus, inflation of the balloon both engages the ports against the wall of the bronchus B and provides the pressure necessary to infuse the neurotoxin fragments into the wall of the bronchus B. Usually, energy will be applied from electrodes 308 or other transducers located within the balloon 304.

Figure 16A:
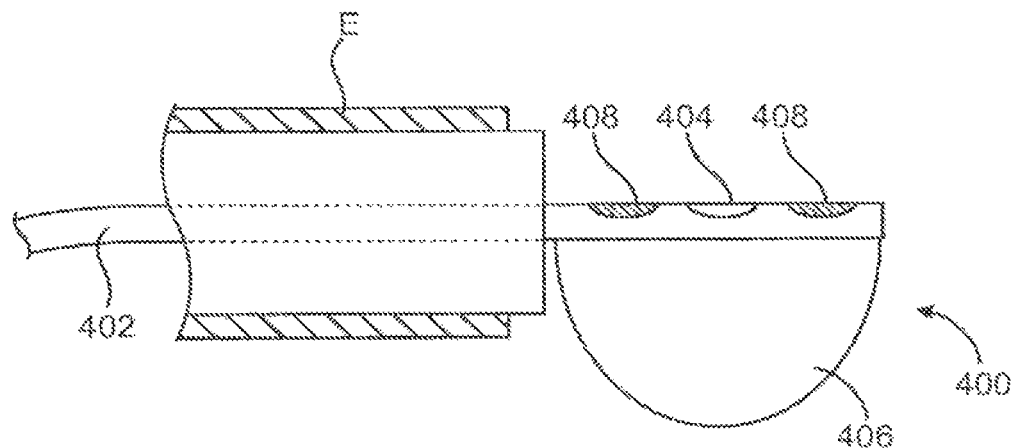
FIGS. 16A and 16B—depict use of a deflected catheter tip for delivering toxin fragments in a lung.
Figure 16B:
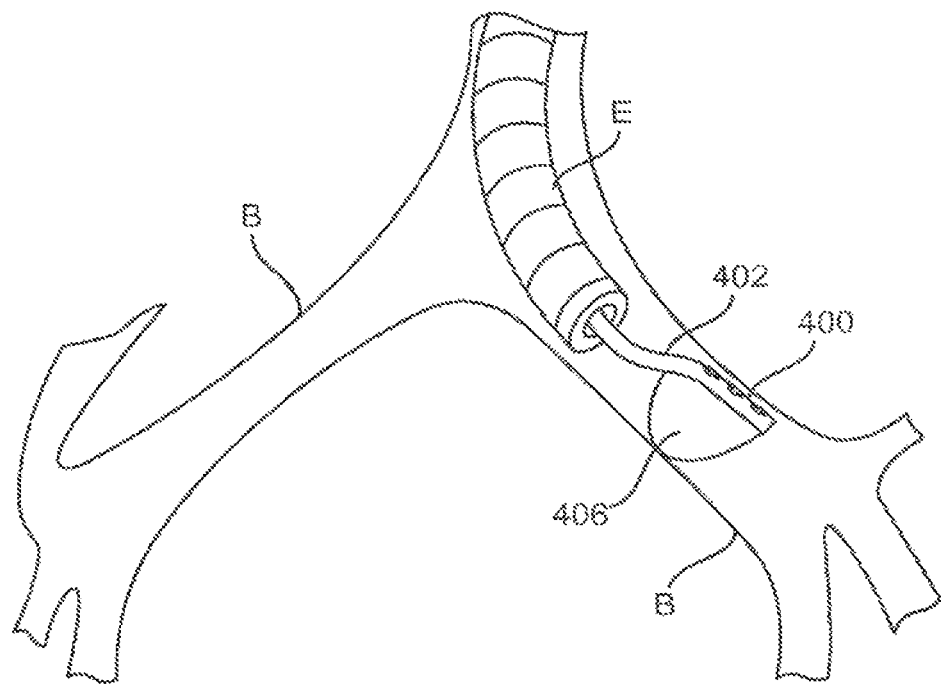

Referring now FIGS. 16A and 16B, the catheter 400 may also be delivered to a bronchus B of a lung through an endoscope E. Catheter shaft 402 terminates with a delivery port 404 near its distal end. A deflection balloon 406 (or other expandable element capable of pressing against the wall of the bronchus B to engage the port 404 against target tissue) is provided on a side of the catheter shaft 402 which is opposite to that of the port 404. Electrodes 408 are provided on either side of the port 404 in order to deliver the poration energy into the target tissue.

Delivery to Nasal Cavity

In other embodiments, the present invention is directed to methods and systems for delivering toxins to target cells within a patient's nasal cavity. The toxins may be intact toxins, such as botulinum toxin, ricin, exotoxin A, diphtheria toxin, cholera toxin, tetanus toxin, other neurotoxins, and active fragments thereof. Each of these toxins comprises a heavy chain responsible for cell binding and a light chain having enzyme activity responsible for cell toxicity.

Botulinum toxin blocks acetylcholine release from cells, such as the epithelial or goblet cells in the nasal membranes responsible for mucus hypersecretion, and can thus be effective even without energy-mediated delivery in accordance with the principles of the present invention. The use of energy to permeablize or porate the cell membranes of the epithelial or goblet cells or other mucus-secreting cells of the nasal lining, in accordance with the present invention, allows botulinum and other toxins to be preferentially delivered to the targeted epithelial or goblet and other mucus-producing cells. Additionally, it allows use of the active or light chains of these toxins (having the heavy chains removed or inactivated) for treatments in accordance with the present invention. Normally, the light chains when separated from the cell-binding heavy chains of botulinum and the other toxins are incapable of entering the cells and thus will be free from significant cell toxicity. By using the energy-mediated protocols of the present invention, the toxin light chains may be locally and specifically introduced into the target cells located within defined regions of the nasal membrane. Thus, even if the toxin fragments are accidentally dispersed beyond the desired target regions, the fragments will not generally enter cells without the additional application of cell permeablizing or porating energy. For that reason, the toxin delivery methods of the present invention are particularly safe when performed with toxin fragments, such as the light chain of botulinum and other toxins.

While the remaining portion of this disclosure will be presented with specific reference to the botulinum toxin light chain, it will be appreciated that the energy-mediated delivery protocols and systems may also be used with other intact toxins and in particular with other light chain toxin fragments as just discussed.

Figure 17:
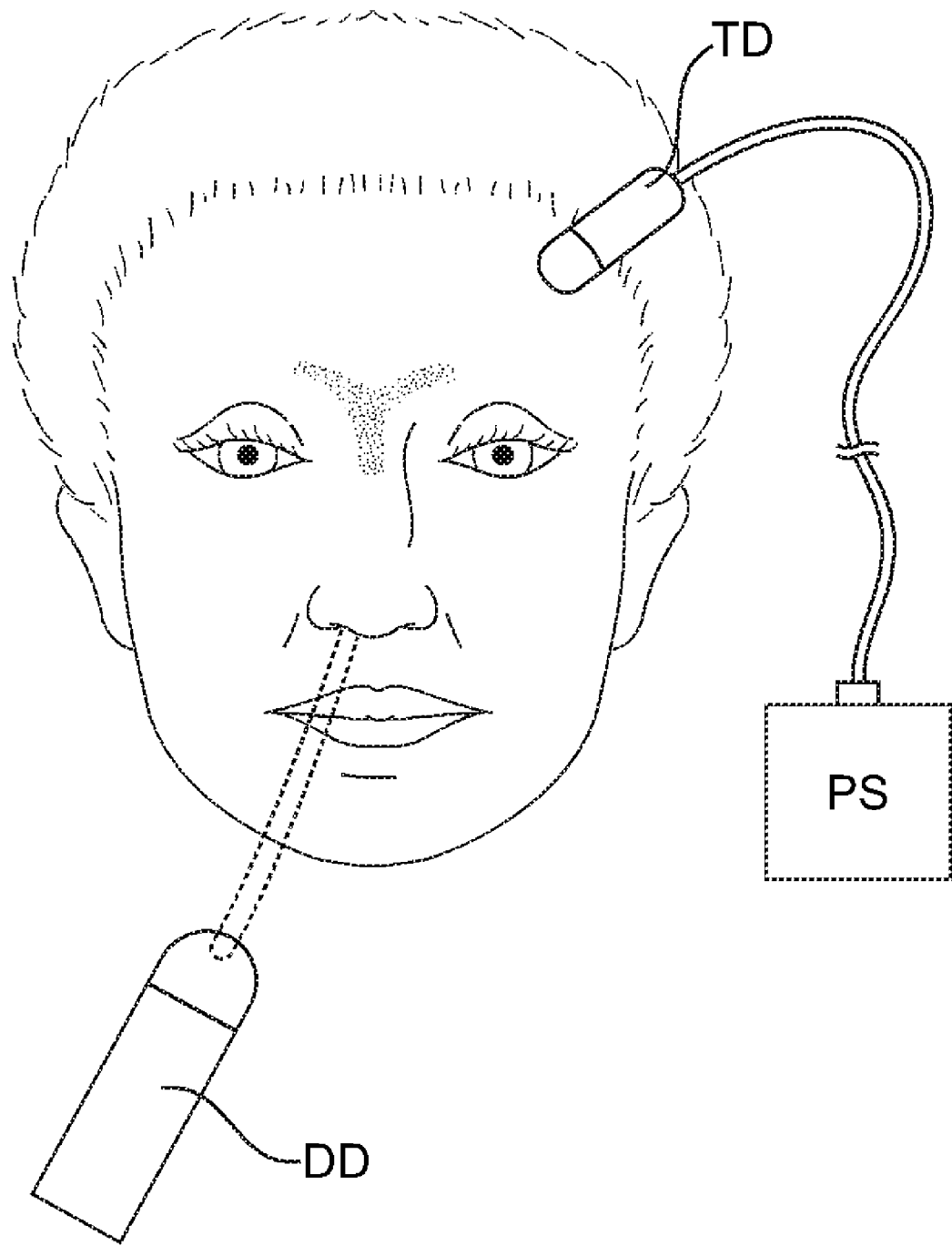
FIG. 17—depicts use on an external hand held transducer for enhancing cellular uptake of toxin delivered from a separate nasal aerosolizer.

It is within the scope of the present invention to deliver the toxin, the energy, or both, non-invasively. For example, as illustrated in FIG. 17, the patient may draw the toxin into the nasal cavity from a hand-held dispersion device DD. After a sufficient amount of the toxin has been infused into the nasal cavity, a separate hand-held transducer TD connected to an appropriate power supply PS will be energized and applied to the nasal cavities by passing the transducer over the appropriate regions of the forehead and nose. Optionally, the transducer can have a focused output so that the acoustic energy is focused in an appropriate depth beneath the skin surface. Typically, from about 0.1 cm to 2 cm.

Figure 18:
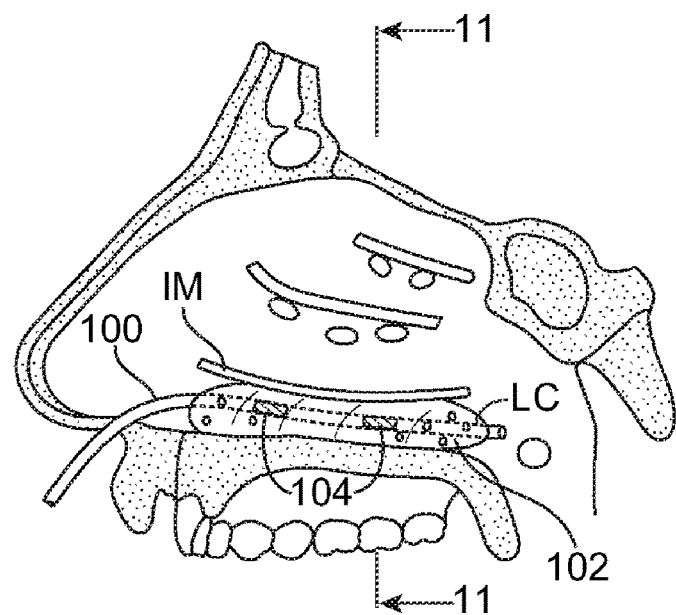
FIGS. 18 and 19—depict use of balloon catheters for delivering toxin to the nasopharynx.

While the toxins and porating energy of the present invention may be delivered to the nasal cavity in a variety of ways, the following provides a number of specific examples of catheters and other structures for delivering toxins to preselected portions of the nasal cavity. For example, as shown in FIG. 18, a balloon catheter 1000 may be provided with a porous balloon 1002 at its distal end. The balloon would be porous over at least a portion of its body so that solution delivered to inflate the balloon, which would contain desired levels of the toxin or toxin fragment, would release the solution through the balloon at a controlled rate. By further providing one or more ultrasonic transducers 1004 within the balloon, optionally mounted on the catheter body, ultrasonic poration energy can be delivered to the adjacent nasal membranes which are receiving the toxin solution. As illustrated in FIG. 18, the toxin is being delivered to a lower surface of the inferior meatus IM to localize and enhance cellular delivery at the balloon tissue interface. Alternatively, the balloon could carry the toxin in a releasable form over its exterior surface in order to deliver to any adjacent tissue structure. In some instances, the toxin could be carried or encapsulated in delivery vesicles which are preferentially fractured by the same acoustic energy which permeablizes the cell wall. Other coatings include hydrogels, such as those produced by Surmodics, Inc., BioCoat, Inc., or the like. In some instances, it may be desirable to provide a coupling agent over and/or within the balloon in order to enhance the delivery of ultrasonic energy from the internal transducer. In still other instances, it would be possible to place polymeric transducers on or within the balloon surface in order to directly deliver ultrasonic or other acoustic energy into the adjacent tissues.

In all the above cases, the ultrasonic transducers can be configured in order to selectively deliver the energy to desired portions of the adjacent tissues. For example, in the embodiment of FIG. 18, the internal transducers 1004 can be configured to focus the ultrasonic energy generally upwardly (as viewed in FIG. 18) in order to preferentially deliver the toxins into the inferior meatus IM while minimizing delivery elsewhere.

As a further option, the balloon could be inflated by a coupling agent in order to enhance the transmission of the ultrasonic or other acoustic energy, while the toxin solution could be infused into the treatment area before or simultaneously using either a separate lumen in the catheter or a separate tube or other delivery catheter. In this way, it would not be necessary to inflate the balloon with a relatively large volume of the toxin solution.

The balloon catheters can be introduced by any conventional technique, for example, in some instances, it may be desirable to use a guidewire to place the catheter into a desired sinus or other location, optionally using fluoroscopic, MRI or ultrasound imaging.

Figure 19:
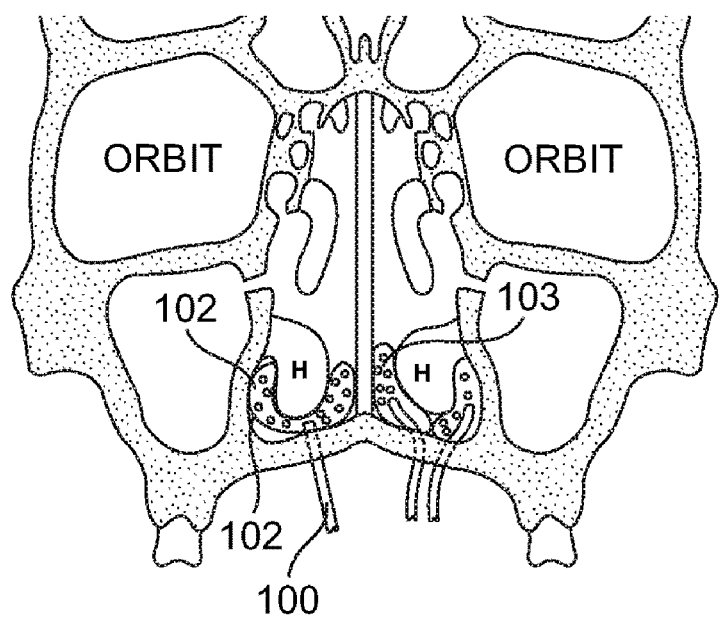

Referring now to FIG. 19, a front view of particular balloons placed as generally shown in FIG. 18, is shown in more detail. A single balloon 1002 can be around the structures H in the inferior meatus. Alternatively, a pair of balloon structures 1003 may be placed in the same space, as shown in the right hand portion of FIG. 19. Optionally, the balloons could be formed from an elastic material, such as a silicone, urethane, latex, thermoplastic elastomers, or other materials where the material is treated to be appropriately porous, for example by laser drilling. Alternatively, the balloons could be formed from non-distensible materials which are pre-formed to conform to the desired target cavities. The non-distensible balloons could also be laser drilled or otherwise made permeable in order to release the toxin solutions of the present invention. Alternatively, either type of balloon could be coated with the toxin solutions, coupling solutions, or other materials which are useful in the protocols of the present invention.

Figure 20A:
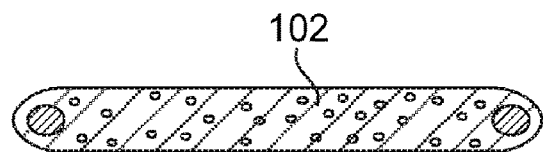
FIGS. 20A-20C—depict use of a self-expanding toxin delivery structure on a catheter.
Figure 20B:
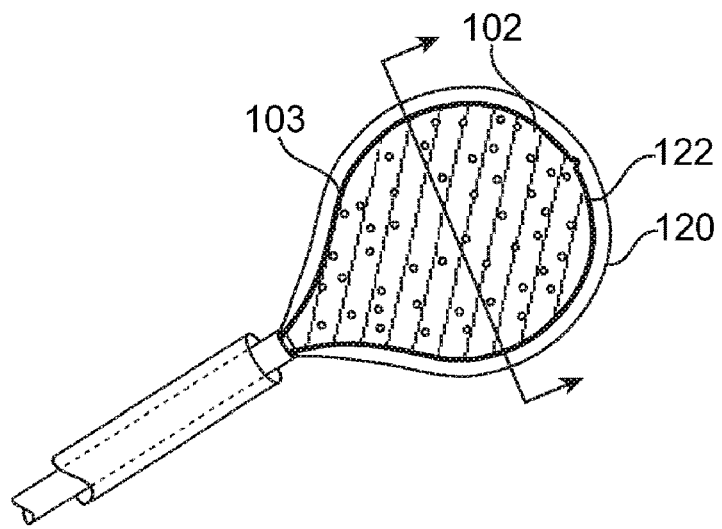
Figure 20C:
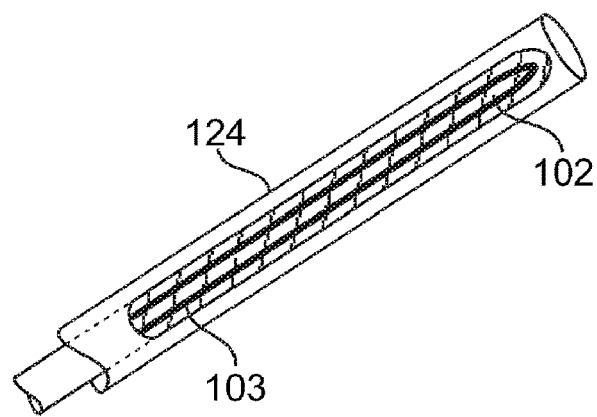

Referring now to FIGS. 20A, 20B, and 20C, as an alternative to inflatable balloons, toxin delivery structures may be made to be various shapes, for example a generally "flattened" balloons 1002, whose profile is narrower in one axis than the other, for example by placement of an internal nitinol or other elastic frame or scaffold, or a stainless steel wire 103 that is fed into the balloon outer structure to form such shape, within a suitable porous cover or membrane. Thus, the structure 1020 may be expanded by the scaffold 1022 after release from a delivery tube 1024. The structures can be used to deliver energy and/or toxin in any of the ways described previously with respect to balloons, including by carrying a transducer or electrode on or within the structure and delivering a toxin solution from the interior of the self-expanding structure through a porous portion of the structure wall.

Figure 21:
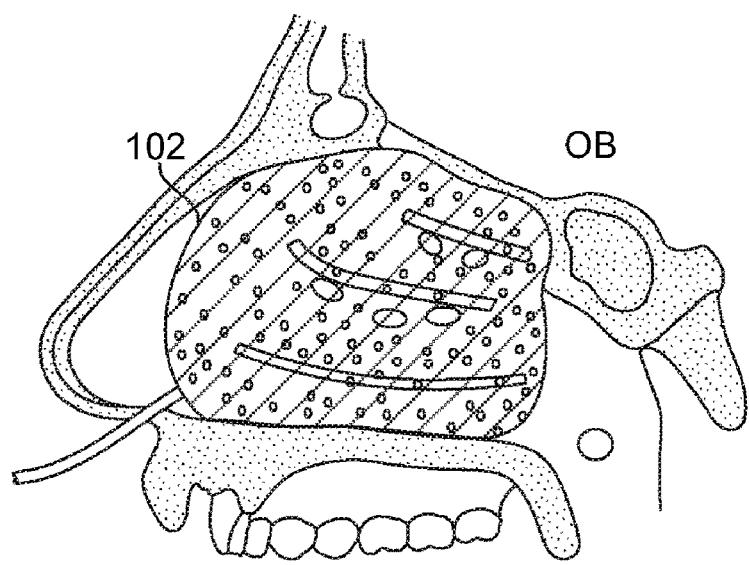
FIGS. 21 and 22—depict a protocol for limiting toxin introduction by partial filling of a porous delivery balloon.
Figure 22:
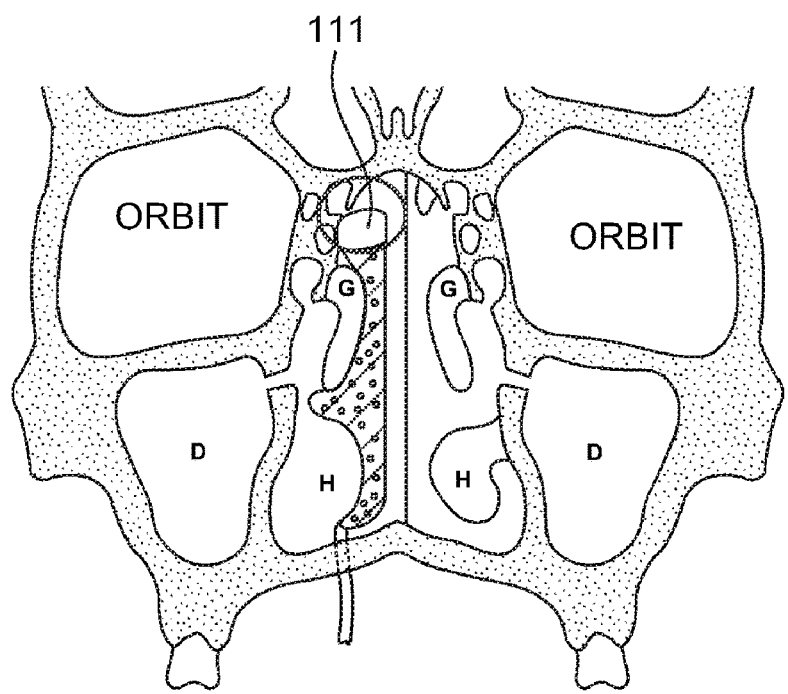

In some instances, it will be desirable to protect the olfactory bulb of the sinuses from treatment with the toxin solutions of the present invention. Referring now to FIGS. 21 and 22, the porous portion of a delivery balloon 1002 can be positioned so that the remaining non-porous segment is in contact with the olfactory bulb (FIG. 21). Thus, when the balloon is inflated and the toxin solution delivered, it will not be directed at the tissues of the olfactory bulb (OB).

As shown in FIG. 22, which is a cross-sectional view of FIG. 21, instead of rendering the top portion of the delivery balloon non-porous, it would be possible to simply refrain from filling the top portion with the toxin solution and/or a coupling solution. This can be achieved by filling the balloon with a known volume of air 1011 in addition to the toxin solution. With the patient positioned appropriately, the air will fill the portion of the balloon in proximity to the olfactory bulb, excluding this tissue from toxin contact. Additionally, the air bubble may act as an ultrasound insulator to inhibit energy delivery to the non-targeted or protected tissue. Thus, delivery of the toxin to the region around the olfactory bulb and/or delivery of the energy to the region around the olfactory bulb can be partially or wholly prevented.

Figure 23:
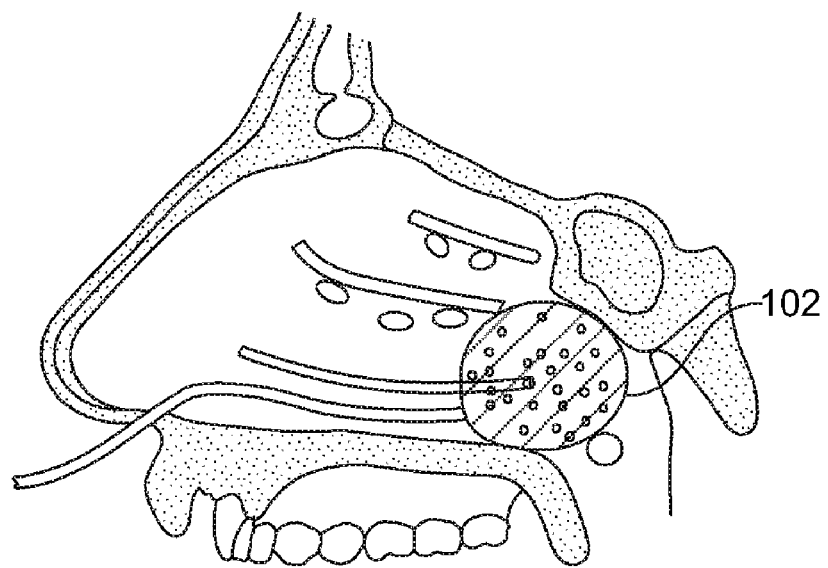
FIGS. 23 and 24—depicts sizing of a delivery balloon to control distribution of toxin released into the nasal cavity.
Figure 24:
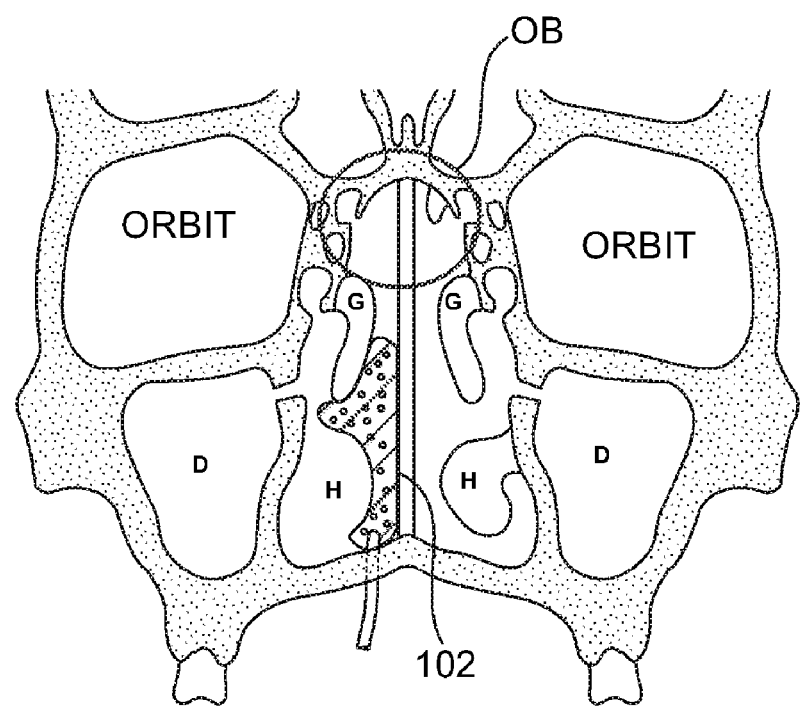

Referring now to FIGS. 23 and 24, the balloon may be sized and positioned to target an area of high goblet cell (G) concentration, for example in the back of the nasal passages in the area of the nasopharynx. By targeting this area of the nasal membrane, a high percentage of mucus-secreting epithelial or goblet cells can be treated with a device which is relatively small and which may carry a relatively low infusion volume and require less energy. Moreover, the olfactory bulb is inherently protected with this technique since the balloon is positioned well away from that area. If desired, of course, additional shielding, shaping or other protective balloons could be positioned between the olfactory bulb and the toxin and energy delivering components of the present invention.

Figure 25:
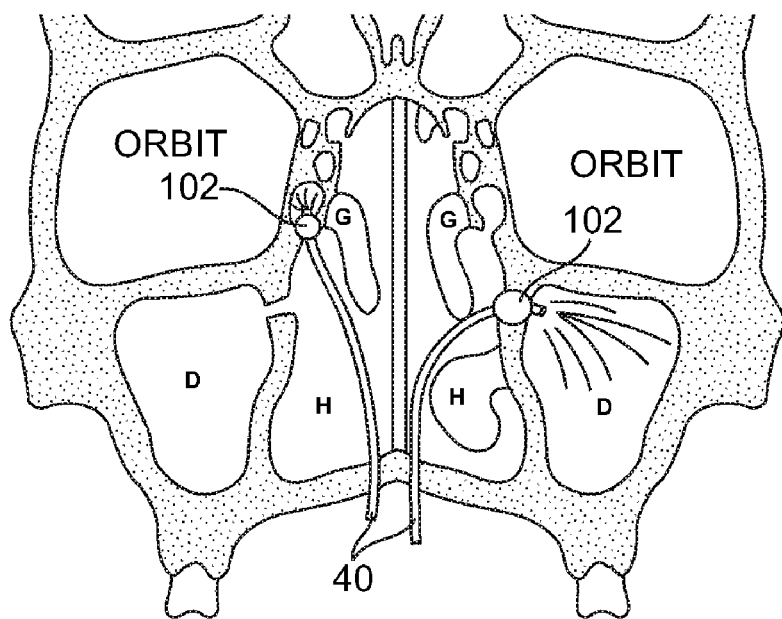
FIG. 25—depicts the use of multiple small balloons for selective toxin delivery into the nasal cavity.

As shown in FIG. 25, direct infusion and treatment of particular sinuses may be effected using relatively small occlusion balloons 1002 which occlude and isolate natural openings into those sinuses. Once the balloon is in place and the occlusion balloon employed, the toxic solution can be delivered by infusion, dispersion, or other conventional techniques. Once the toxin solution is present in the sinus, all or a portion of the membrane of the sinus can then be treated with an external or other ultrasonic source.

Figure 26:
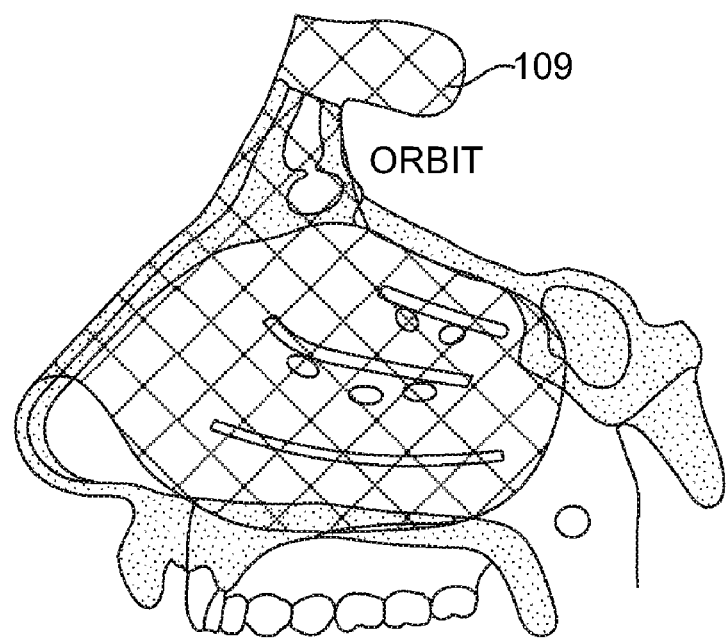
FIG. 26—depicts sonoporation using an external mask placed over the sinuses and nose.
Figure 27:
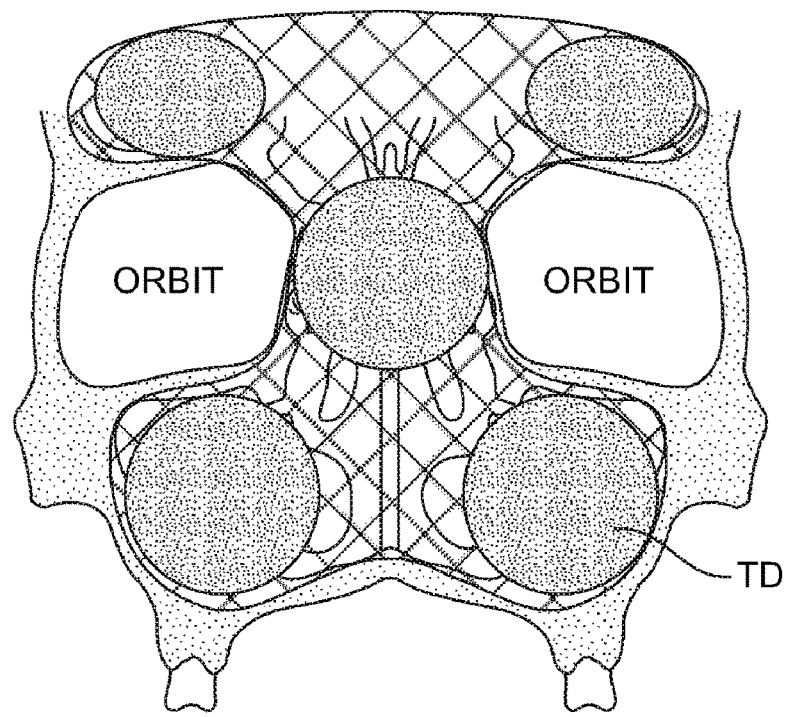
FIG. 27—depicts a front view of an external sonoporation mask showing placement of ultrasound transducers.

For example, as shown in FIGS. 26 and 27, the external transducer may comprise a mask which conforms to the nose and optionally over the sinuses, where the mask carries one or more ultrasonic or other acoustic transducers (TD) adapted to deliver energy transcutaneously into the sinuses. The mask may comprise a plurality of individual transducers (TD), which may be made from one, two, or several generally continuous piezoelectric films which are formed over or lamented within the mask. Alternatively, multiple individual piezoelectric crystal transducers can be built into the mask.

The effect of such externally applied ultrasonic energy can be enhanced by introducing microbubbles (free air) into the isolated sinuses and/or nasal passages which have been filled with toxin solution. For example, encapsulated microbubbles, which are generally useful as echocardiographic contrast agents, or specialty perfluorocarbons, are useful as such ultrasonic enhancing agents. By encapsulating the toxin molecules in spheres or bubbles, or by simply placing the spheres or bubbles in proximity to toxin molecules, the ultrasonic or other acoustic energy can be captured and stored until it is abruptly released with fracture of the sphere or bubble. Such microspheres will also act as resonance bodies as defined below.

Figure 28:
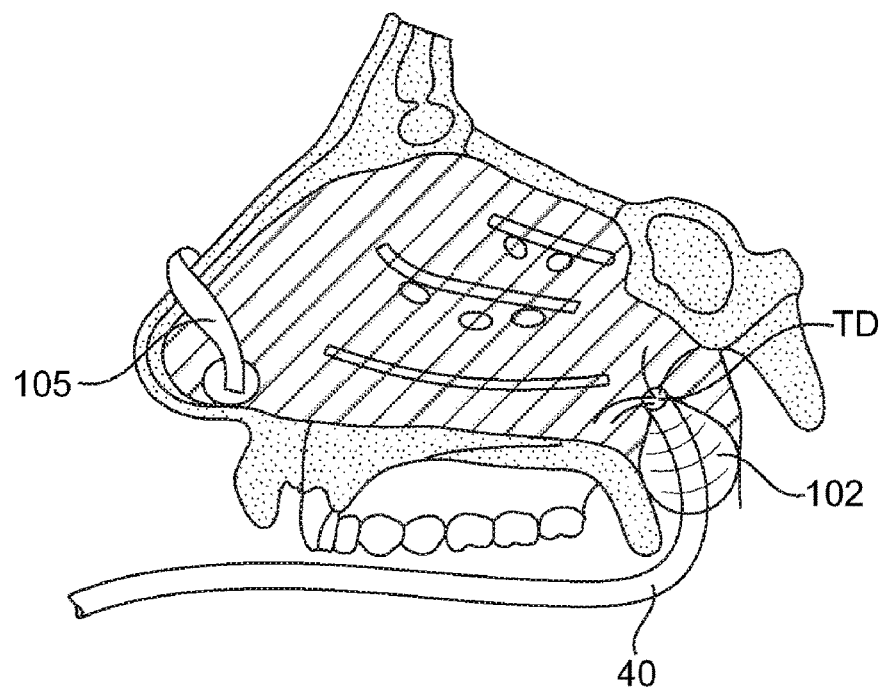
FIGS. 28 and 29—depict an orally-introduced occlusion catheter and energy applicator system.
Figure 29:
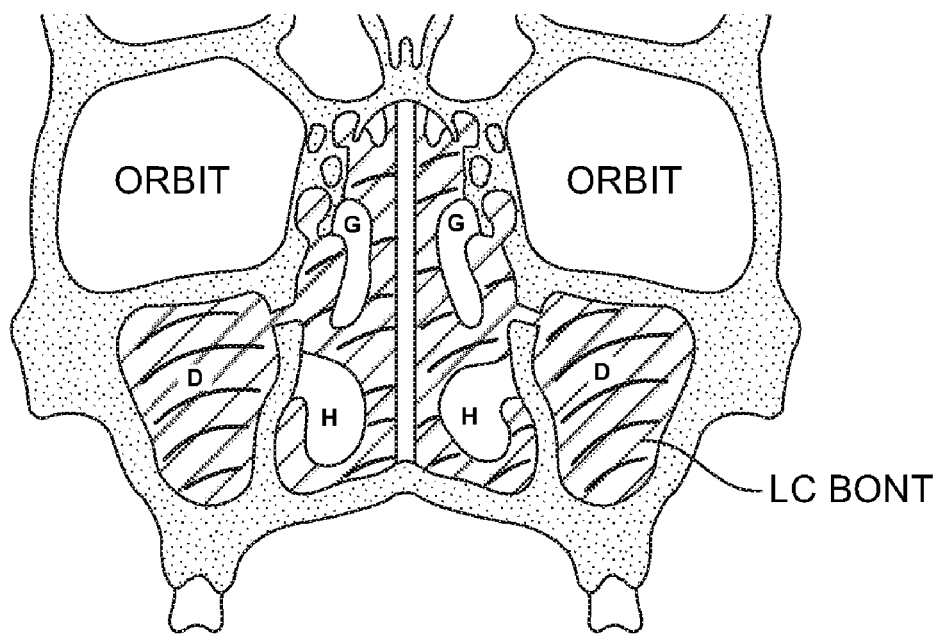

Referring now to FIGS. 28 and 29, a catheter 400 is placed at the posterior outlet of the nasal passages in the region of the nasopharynx. The catheters configured to occlude outflow from these sinuses and passages into the throat. As shown in FIG. 28, a balloon catheter 1002 or other occlusion device could be configured to block such passage. As shown in FIG. 28, the catheter is delivered in through the mouth and guided into the posterior portion of the nasal cavities, typically using a guidewire. Once the nasopharynx of the posterior portion of the nasal cavity is occluded, toxin solution (BoNT) can be infused through the occluding catheter lumen, or through a separate infusion catheter or tube, in order to treat substantially the entire sinus and/or nasal cavity membrane at once (FIG. 29). When the toxin solution is introduced through the catheter at the posterior region of the cavities, it will frequently be desirable to occlude the nostrils, for example using a nasal clip 1005.

Figure 30:
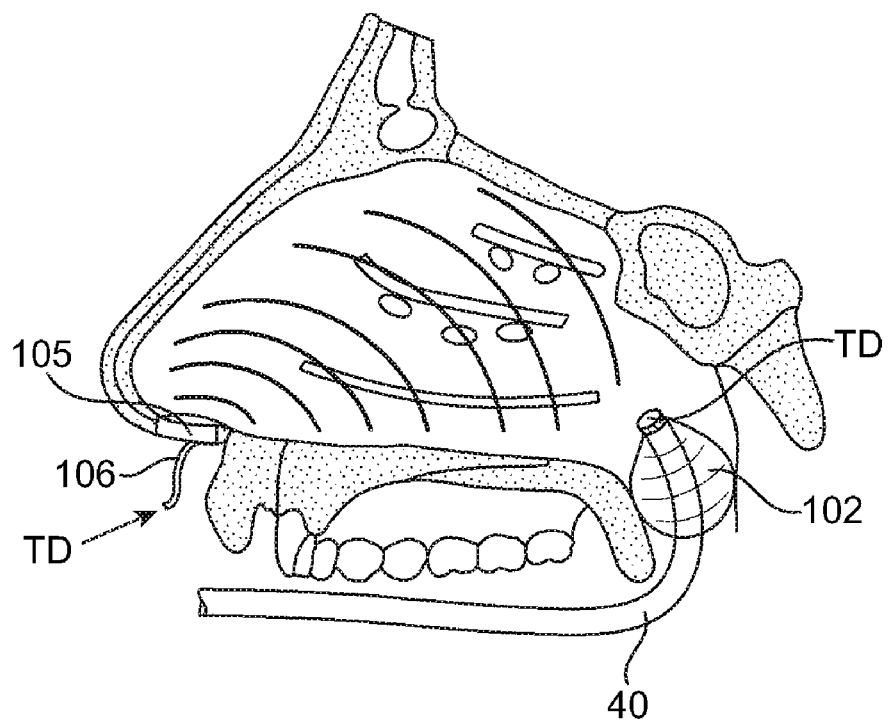
FIGS. 30 and 31—depict nose plugs for occluding and optionally delivery poration energy to the nasal cavity.
Figure 31:
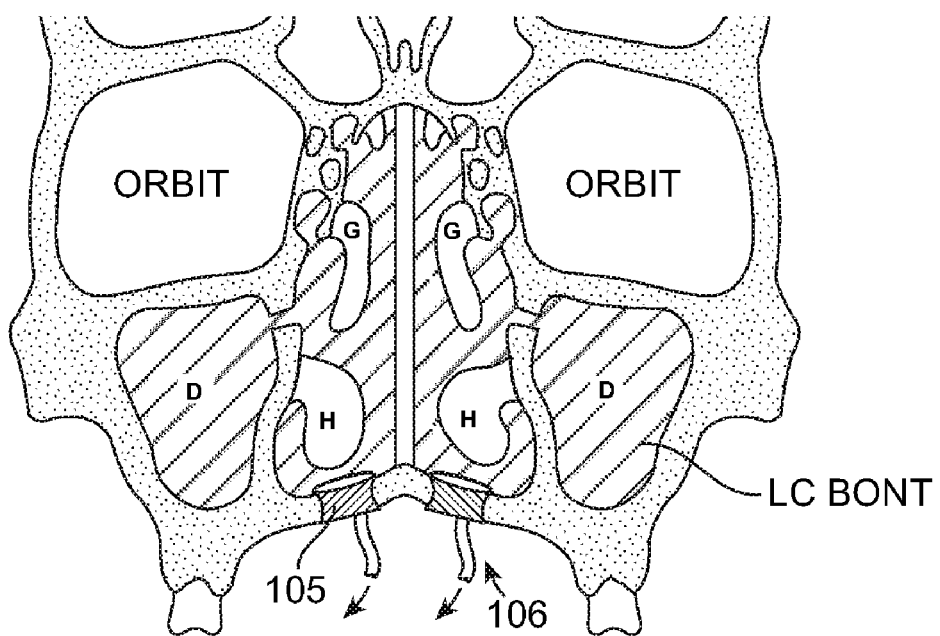
Figure 32:
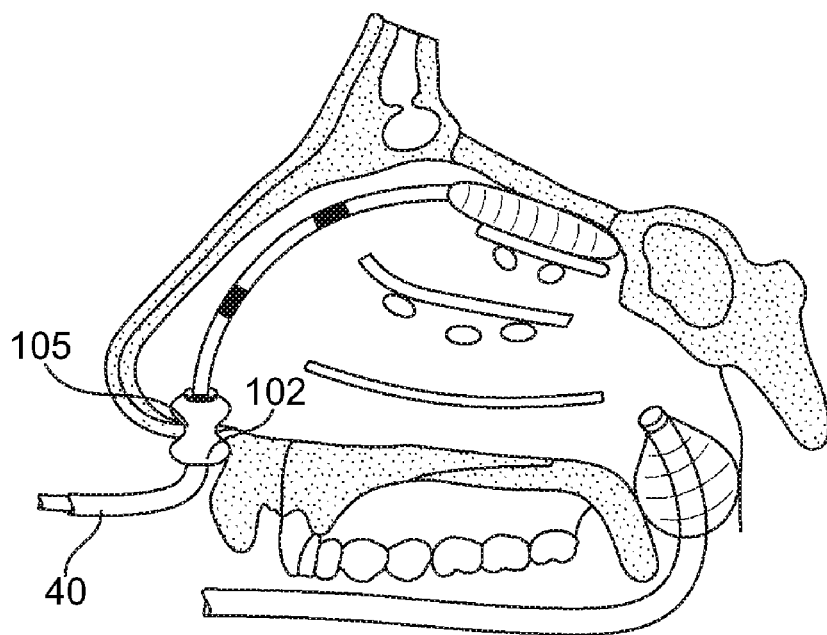
FIGS. 32 and 33—depict an alternate occlusion catheter system for targeted toxin delivery to the nasopharynx.

As shown in FIGS. 30 and 32, specially designed nose plugs 1005 can be provided with air bleed valves 1006 which are used to occlude the nostrils in order to evacuate or bleed air from the nasal passages while filling the passages with the toxin solution. The nose plugs 1005 could optionally include ultrasonic transducers in order to deliver ultrasonic or other acoustic energy into the solutions entrapped within the nasal cavities using the nostril plugs. Alternatively, of course, the ultrasound or other acoustic energy could be delivered from an external transducer as described previously.

Figure 33:
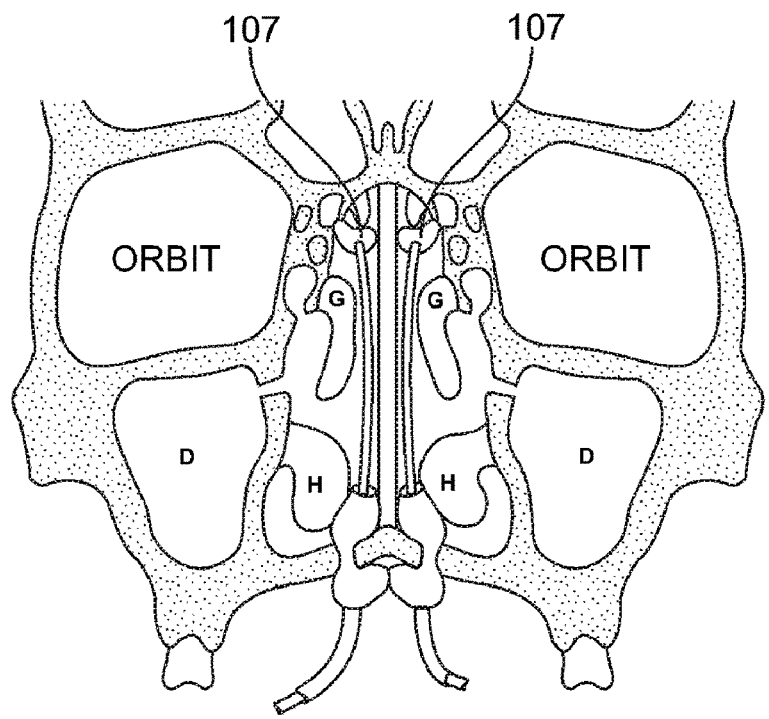

Referring now to FIGS. 32 and 33, an alternate occlusion catheter system for nasopharynx occlusion is illustrated. An occlusion catheter 400 is introduced through a nostril, where the tip includes an ultrasonic transducer to provide sonoporation. A nostril plug 1005 is provided proximally on the shaft of the catheter, while the cavity is blocked with a separate occlusion balloon 1002 introduced through the mouth and into the posterior nasopharynx region. The toxin solution can be introduced into the cavity through either the catheters which pass through or reside in the nostrils or the catheter which occludes the posterior nasopharynx.

Figure 34:
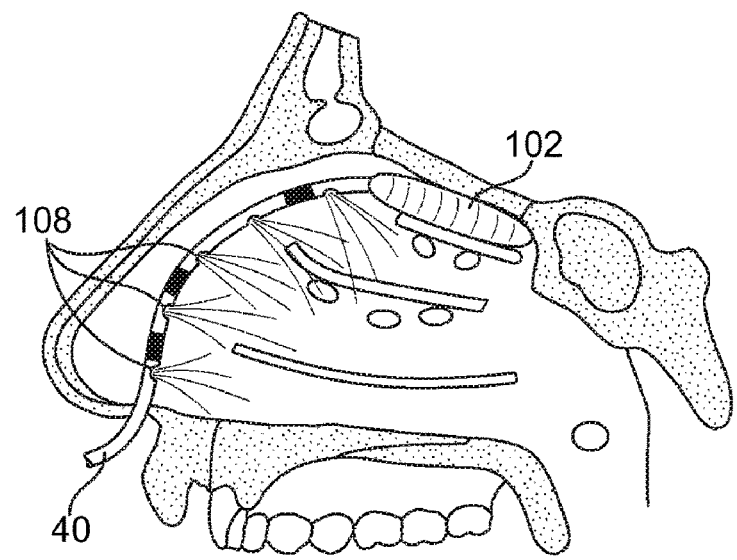
FIGS. 34 and 35—depict use of a toxin delivery catheter having side holes and a distal occlusion balloon for isolating and protecting the olefactory bulb.
Figure 35:
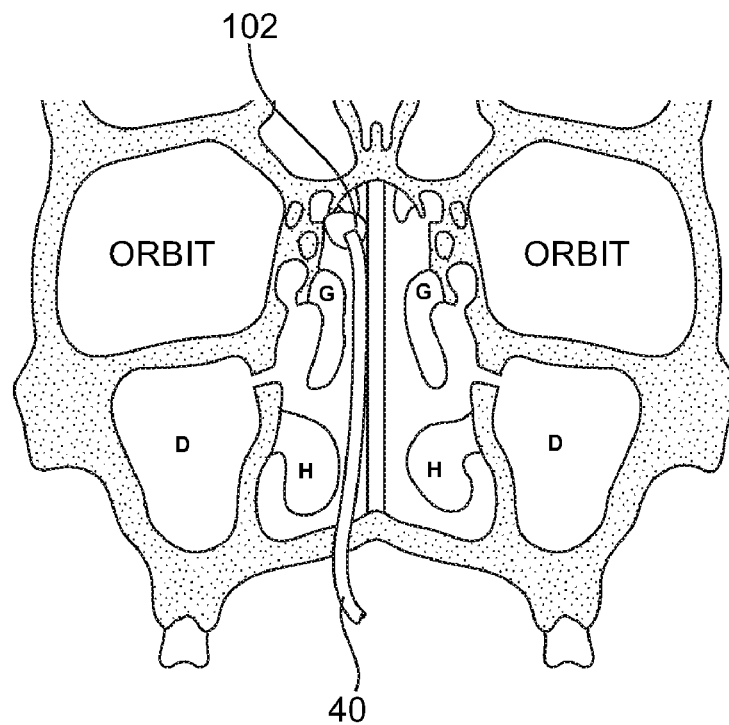

FIGS. 34 and 35 illustrate how a catheter 400 with side holes 1008 can be configured to deliver toxin away from the olfactory bulb, even when used alone without separate nasopharynx occlusion catheters. The catheters preferably carry an occlusion balloon or other structure near their distal ends 1007 to prevent or inhibit toxin from reaching the olefactory bulb.

Use of these or other catheter devices can deliver toxin incorporated into vesicles which may be configured as "resonance" bodies, which reduce the need to fill the nasal cavities with a liquid or other form of toxin. For example, lipid microspheres which incorporate the toxin may be sprayed or aerosolized onto target surfaces of the nasal epithelium. After the lipid or other resonance bodies are attached to the targeted epithelium membrane surface(s), the ultrasound energy can be delivered from the catheter or externally through the skin in order to selectively porate the epithelial or goblet cells to enhance introduction of the toxin vis-à-vis resonance bodies. A protection device at the end of the shaft can be provided to shield the olfactory bulb from the toxin.

Figure 37:
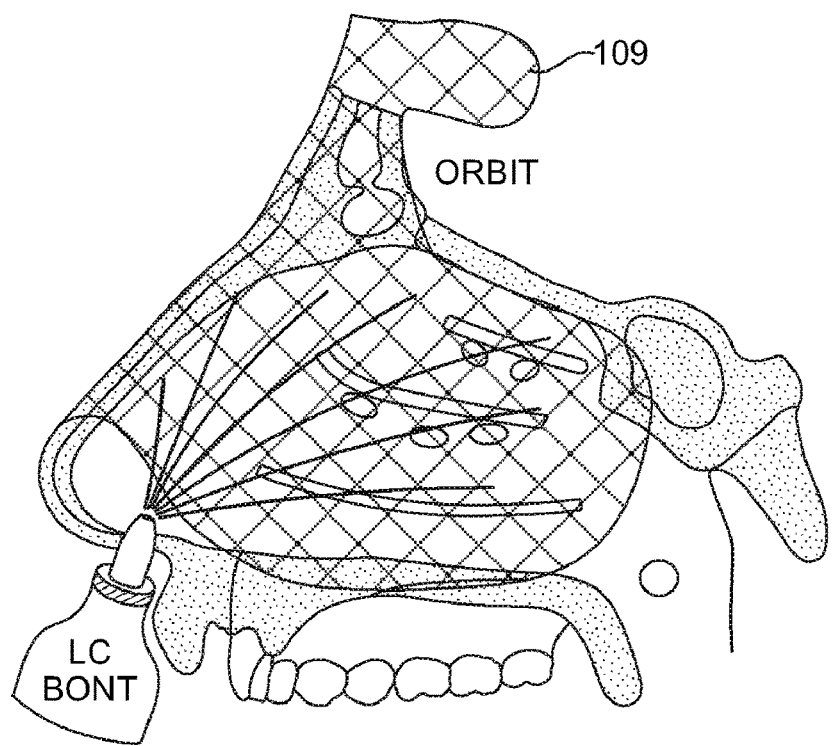
FIG. 37—depicts toxin delivery using a nasal spray and energy delivery using a face mask.

Referring to FIG. 37, the toxin may be delivered as a conventional nasal spray (BoNT), as mentioned hereinbefore, and the poration energy can be delivered through a face mask. The poration energy might alternatively be delivered as ultrasound energy delivered through a mist, without direct contact to the tissues. This mist might be the same mist which contains the toxin, or it might be a different, possibly denser mist delivered at some time after the toxin has been delivered. The delivery devices for these mists might be introduced a relatively short distance into the nose. Thus the entire therapy might comprise the specialized delivery of two mists.

Figure 36:
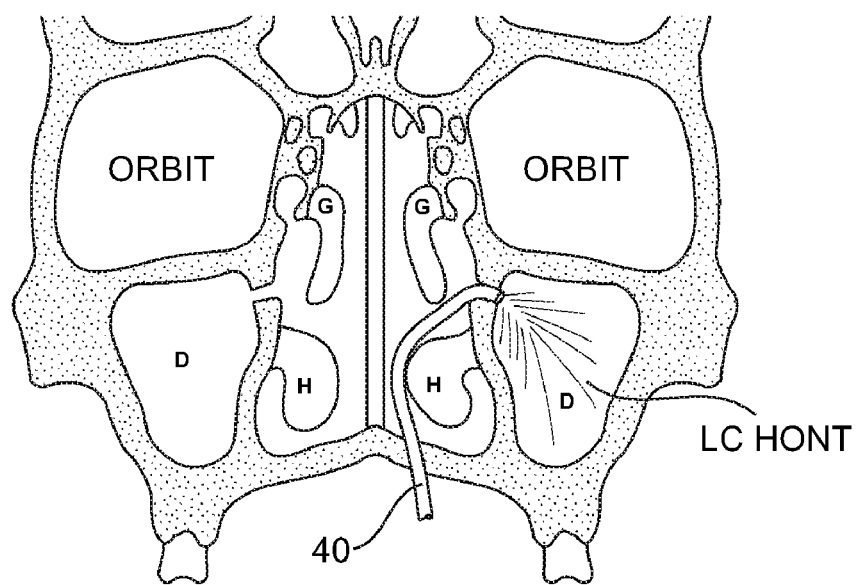
FIGS. 36 and 38—depict use of a simple catheter having a shaped distal end for aerosolizing a toxin into a target nasal sinus though an ostium open to the sinus.
Figure 38:
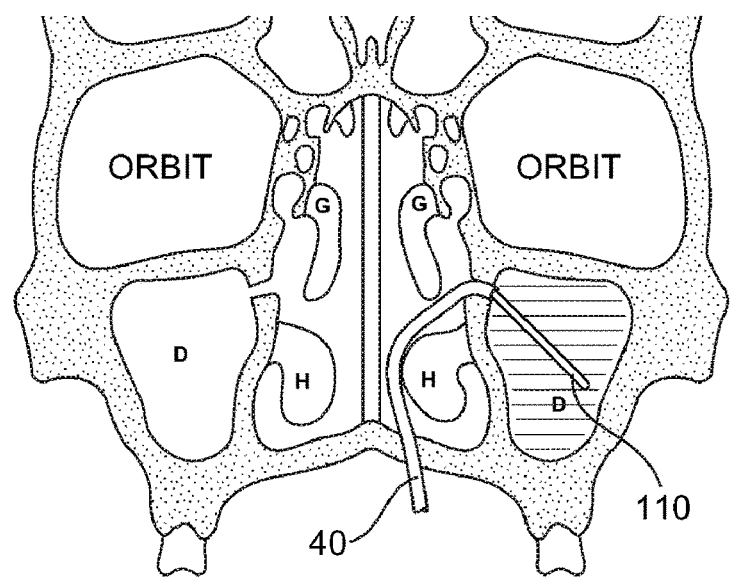

Referring now to FIGS. 36 and 38, an infusion catheter 400 can be engaged against the ostium of a sinus cavity (FIG. 36). A guidewire 1010 may then be advanced through the infusion catheter and into the sinus cavity (FIG. 38). The guidewire can be formed as a wave guide to deliver ultrasonic energy, as an electrode to deliver electroporation energy, or as an infusion wire to deliver the toxin solution itself. The wire could further be configured to perform two or more of these functions. The catheter could be configured to act as a counter electrode when the guidewire is acting as an electroporation electrode in bipolar energy delivery.

Figure 39:
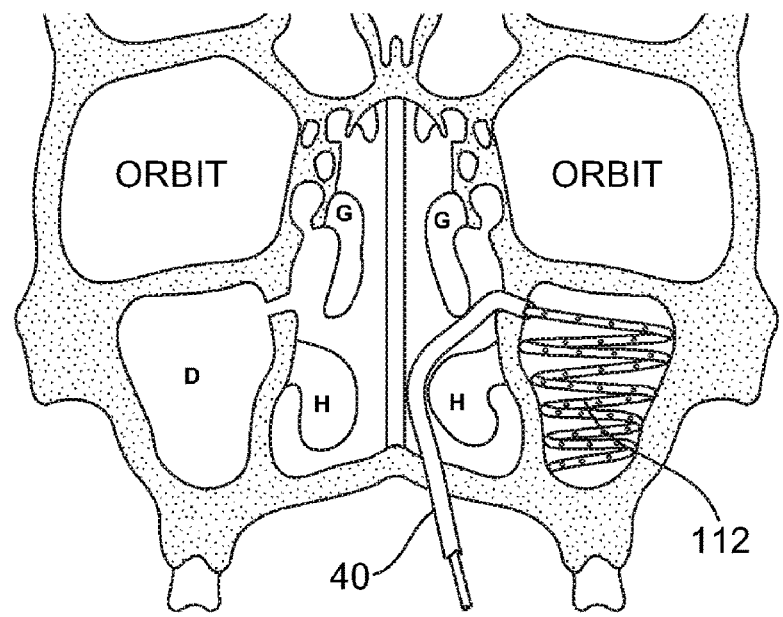
FIGS. 39 and 40—depict use of a catheter having a shaped distal end for positioning separate infusion structures with a target sinus cavity.

Referring now to FIG. 39, the catheter advanced to the os of a sinus cavity, as illustrated, can also be used to deliver a helical or randomly shaped delivery tube 1012 which is deployed within the sinus. Preferably, the tube will expand to engage a major portion of the wall of the sinus cavity. Alternatively, the geometry could be selected to selectively engage only a particular portion of the wall of the sinus cavity. The wire can further be adapted to deliver energy, either electrical or acoustic, and/or may be configured to deliver and distribute the toxin solution within the cavity. In still other configurations, the wire could be coated to deliver the agent to the wall, and still further the wire could deliver ultrasound gels, saline, degassed water, or the like, to enhance coupling of a separate ultrasonic energy source.

Figure 40:
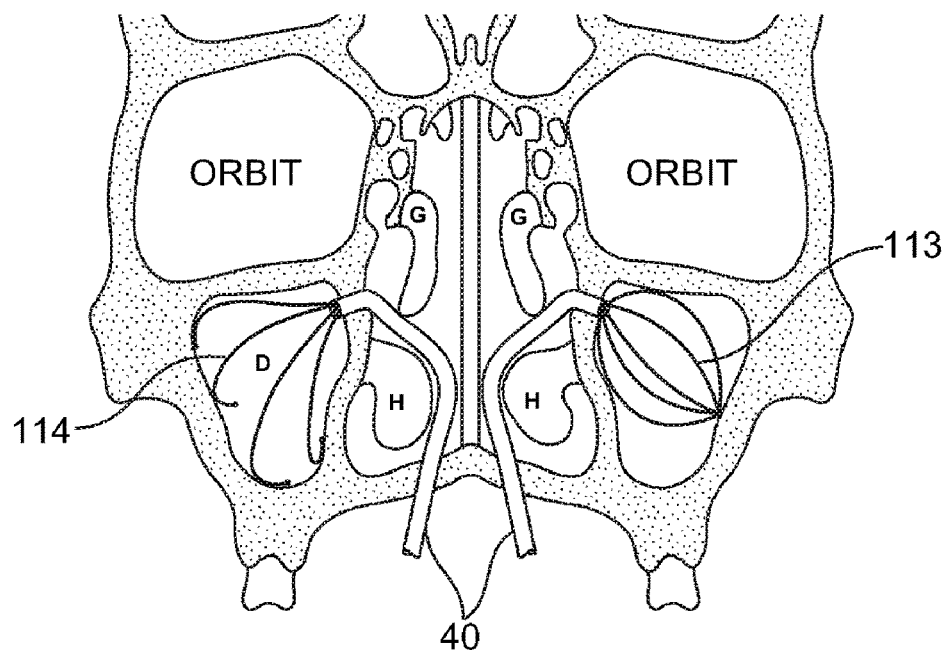

Referring now to FIG. 40, two or more deployment catheters can be used to advance any of the guidewires or other wire structures discussed above. As illustrated in FIG. 40, an electrode basket 1013 may be deployed through the delivery catheter. Alternatively, a multiply tined catheter 1014 structure may be delivered through the delivery catheter.

Throughout this disclosure, the LC solution has typically been referred to as an infused, aerosolized or sprayed liquid. LC incorporated into coatings on devices has also been described. It should be noted, however, that other forms of LC delivery may be desirable.

For instance, commercially available botulinum toxins (such as Botox™—Allergan) are supplied as a dry lyophilized powder, and must be reconstituted prior to delivery by the addition of saline to the packaging vial. Similarly, light chain would be most readily available and stable in a powdered form. It may be desirable to spray or blow the powdered form of the LC into the target airways directly, without any reconstitution by liquid.

The lyophilized powder could also be formed into sheets, ribbons, pellets microspheres, or any other desirable form, and introduced to the target tissues.

Instead of a saline or low viscosity carrier, it may be desirable to deliver the light chain in a gel carrier, such as the types of gels which are commonly used for ultrasound coupling. Other appropriate gel carriers include such biocompatible gels as hyaluronic acid (HA). HA has the added benefit of being a thixotropic liquid—its viscosity drops as it begins to flow or as increasing shear stress is applied, and then returns to a higher viscosity state as it comes to rest. This would aid in delivery of the solution through catheters and the like, while allowing the gel to remain in place once delivered. HA is also extremely biocompatible, and would allow efficient ultrasonic coupling to the target tissues. The application of ultrasonic energy might also reduce the viscosity of the HA gel, possibly improving the delivery of toxin into the tissues.

It may also be desirable to incorporate the light chain into a foam, or to foam the LC solution upon or during delivery of the LC to the target tissues. Foams may better fill the entire targeted airway, and may trap water or coupling agents to allow efficient ultrasonic coupling. In a further embodiment, the foam may be energized within or as it exits the catheter shaft to further enhance the delivery of the LC to cells that are contacted by the energized foam and LC foam solution.

In addition to BTX-LC, it may be desirable to deliver additional agents to the nasal passages and sinuses prior to, coincident with, or after delivery of the LC. Adjunctive therapies may include agents designed to slow down or halt the motion of the cilia, in order to aid in delivery of the LC to the target tissues by prevention of their mobilization by the cilia. Agents known to slow or halt the motion of cilia include but are not limited to epinephrine dilutions of 1:1000 (which causes ciliary death), 1:10,000 (which causes reversible paralysis), 10% cocaine (induces paralysis) or 2.5% cocaine (slows or stops cilia).

Other adjunctive therapies may include the use of or pretreatment with mucolytics, which will thin mucus secretions within the nose and may allow better penetration of LC into the target cells.

Decongestants such as epinephrine also cause constriction of the vasculature in the nasal passages, which in addition to temporarily reducing swelling of the target tissues, may decrease the risks of LC entering the blood stream during poration and delivery. Epinephrine also constricts the blood vessels locally, which may increase the residence time of other locally delivered agents or decrease their likelihood of entering systemic circulation.

Steroids may be used to reduce swelling and inflammation prior to LC treatment in order to improve LC delivery to target tissues. In the abovementioned embodiments, it may be important to note that by far the most significant effects will be seen in areas where both the LC and the permeablizing energy are delivered. Therefore, although it may be best to deliver both LC and energy to substantially the same area, for reasons of anatomy, ease of delivery, etc., either the LC or the energy might be delivered more broadly, or to a somewhat different area. As an extreme example, the LC might be delivered systemically or to the entire respiratory pathway, followed by very localized delivery of energy to the desired area. Alternatively, the LC could be delivered to a specific sinus, followed by energy to the entire nose and sinus using a standardized external energy delivery mask.

Although various illustrative embodiments of the present invention are described above, it will be evident to one skilled in the art that various changes and modifications may be made without departing from the scope of the invention. It will also be apparent that various changes and modifications may be made herein without departing from the invention. The appended claims are intended to cover all such changes and modifications that fall within the true spirit and scope of the invention.

What is claimed is:

1. An apparatus for treating rhinitis in a nasal cavity, the apparatus comprising:
- an elongate body, comprising:
  - a proximal portion; and
  - a distal portion configured for positioning in the nasal cavity;
- multiple radiofrequency electrodes coupled with the distal portion of the elongate body; and
- a radiofrequency generator coupled with the proximal portion of the elongate body for supplying radiofrequency energy to the multiple radiofrequency electrodes to treat a target tissue in the nasal cavity and thus treat rhinitis.

2. The apparatus of claim 1, wherein the multiple radiofrequency electrodes comprise at least two bipolar radiofrequency electrodes.

3. The apparatus of claim 2, further comprising at least one sensing electrode.

4. The apparatus of claim 2, wherein the at least two bipolar radiofrequency electrodes comprise multiple pairs of bipolar radiofrequency electrodes.

5. The apparatus of claim 1, wherein the target tissue comprises nerve tissue.

6. The apparatus of claim 1, wherein at least one of the multiple radiofrequency electrodes is movable relative to the distal portion of the elongate body.

7. The apparatus of claim 1, wherein the multiple radiofrequency electrodes are configured to deliver energy laterally relative to the distal portion of the elongate body.

8. The apparatus of claim 1, wherein at least one of the multiple radiofrequency electrodes is configured to extend laterally from the distal portion of the elongate body.

9. The apparatus of claim 7, wherein the at least one of the multiple radiofrequency electrodes is configured to penetrate nasal mucosa lining the nasal cavity.

10. The apparatus of claim 1, further comprising a thermocouple coupled with the distal portion of the elongate body for sensing temperature of a nasal tissue in the nasal cavity.

11. The apparatus of claim 1, further comprising a monitoring system coupled with the distal portion of the elongate body for monitoring a degree of treatment of the target tissue.

12. The apparatus of claim 1, further comprising an agent delivery element coupled with the distal portion of the elongate body for delivering a therapeutic agent to the target tissue.

13. The apparatus of claim 12, wherein the agent delivery element comprises at least one needle.

14. The apparatus of claim 13, further comprising a source of the therapeutic agent coupled with the proximal portion of the elongate body.

15. The apparatus of claim 14, wherein the therapeutic agent comprises a neurotoxin.

* * * * *